United States Patent
Flynn, Sr.

(10) Patent No.: US 9,126,004 B2
(45) Date of Patent: Sep. 8, 2015

(54) MULTIPURPOSE THERAPEUTIC FACE MASK

(71) Applicant: Stephen Donald Flynn, Sr., Oakville (CA)

(72) Inventor: Stephen Donald Flynn, Sr., Oakville (CA)

(*) Notice: Subject to any disclaimer, the term of this patent is extended or adjusted under 35 U.S.C. 154(b) by 163 days.

(21) Appl. No.: 13/920,046

(22) Filed: Jun. 17, 2013

(65) Prior Publication Data

US 2013/0276784 A1    Oct. 24, 2013

Related U.S. Application Data

(63) Continuation of application No. 12/423,615, filed on Apr. 14, 2009, now Pat. No. 8,464,715.

(60) Provisional application No. 61/045,304, filed on Apr. 16, 2008.

(51) Int. Cl.

| | |
|---|---|
| *A62B 9/02* | (2006.01) |
| *A61M 16/06* | (2006.01) |
| *A61M 16/08* | (2006.01) |
| *A61M 16/20* | (2006.01) |
| *A61M 16/00* | (2006.01) |
| *A61M 16/10* | (2006.01) |
| *A61M 16/14* | (2006.01) |
| *A61M 11/02* | (2006.01) |
| *A61M 11/06* | (2006.01) |
| *A61M 15/00* | (2006.01) |

(52) U.S. Cl.
CPC ............ *A61M 16/06* (2013.01); *A61M 16/0078* (2013.01); *A61M 16/0816* (2013.01); *A61M 16/0833* (2014.02); *A61M 16/105* (2013.01); *A61M 16/107* (2014.02); *A61M 16/1065* (2014.02); *A61M 16/14* (2013.01); *A61M 16/208* (2013.01); *A61M 11/02* (2013.01); *A61M 11/06* (2013.01); *A61M 15/009* (2013.01); *A61M 2202/0208* (2013.01); *A62B 9/02* (2013.01)

(58) Field of Classification Search
CPC ............ A61M 16/0816; A61M 16/20; A61M 16/206; A61M 16/208; A62B 9/02
USPC ............ 128/203.28, 203.29, 204.18, 205.13, 128/205.17, 205.24, 205.25, 206.12, 128/206.21, 206.28, 207.12, 912
See application file for complete search history.

(56) References Cited

U.S. PATENT DOCUMENTS 3,088,477 A * 5/1963 Bloom ........................ 137/512.2
3,262,446 A * 7/1966 Stoner ....................... 128/205.13

(Continued)

*Primary Examiner* — Lynne Anderson
*Assistant Examiner* — Kathryn E Ditmer
(74) *Attorney, Agent, or Firm* — Steven M. Greenberg; CRGO Law

(57) ABSTRACT

A therapeutic face mask comprises a face-engaging portion and a single connector having a mask-engaging end and a single treatment-receiving end which has a single attachment mounting for detachably sealingly receiving a treatment attachment, such as an oxygen reservoir bag or a nebulizer. A one-way inhalation valve in the connector permits fluid flow from the treatment-receiving end to the mask-engaging end during inhalation and inhibits fluid flow in the other direction. The mask also includes a valve-governed exhalation port and an anti-asphyxia valve assembly configured to permit fluid flow from ambient to the face-engaging portion during inhalation only when inspiratory effort during inhalation exceeds fluid flow to the treatment-receiving end of the connector. Also provided is an oxygen reservoir bag having a neck shaped for removable coupling to a mating connector of a therapeutic face mask. An oxygen reservoir bag may have a metered-dose inhaler port defined in its neck.

6 Claims, 19 Drawing Sheets

(56) References Cited

U.S. PATENT DOCUMENTS

| | | | |
|---|---|---|---|
| 3,467,093 A * | 9/1969 | Hotz et al. | 128/206.24 |
| 3,527,242 A * | 9/1970 | Ansite | 137/102 |
| 3,726,274 A * | 4/1973 | Bird et al. | 128/205.24 |
| 3,882,860 A * | 5/1975 | Frimberger | 128/202.16 |
| 4,064,875 A * | 12/1977 | Cramer et al. | 128/202.22 |
| 4,501,271 A * | 2/1985 | Clifton et al. | 128/205.13 |
| 4,622,964 A * | 11/1986 | Flynn | 128/205.24 |
| 5,020,530 A * | 6/1991 | Miller | 128/203.28 |
| 5,217,006 A * | 6/1993 | McCulloch | 128/205.13 |
| 5,394,867 A * | 3/1995 | Swann | 128/201.25 |
| 8,464,715 B2 | 6/2013 | Flynn, Sr. | |
| 2008/0078395 A1 * | 4/2008 | Ho et al. | 128/205.24 |
| 2008/0223457 A1 * | 9/2008 | Kobziar et al. | 137/493 |

\* cited by examiner

MULTIPURPOSE THERAPEUTIC FACE MASK

CROSS-REFERENCE TO RELATED APPLICATIONS

This application is a Continuation of U.S. application Ser. No. 12/423,615, filed Apr. 14, 2009, entitled "MULTIPURPOSE THERAPEUTIC FACE MASK," which claims priority to and is a non-provisional application of provisional Application No. 61/045,304 filed on Apr. 16, 2008, the entirety of which is incorporated herein by reference.

FIELD OF INVENTION

The invention relates to therapeutic face masks, and more particularly to a therapeutic face mask which can be selectively configured to supply a patient with oxygen from a pressurized source thereof, and to supply a patient with medication.

BACKGROUND OF THE INVENTION

There are various medical conditions which require a patient to be supplied with oxygen, either as pure oxygen or mixed with ambient air in a required ratio. It may also be necessary to supply medication to a patient's mouth without removing the face mask. Further, it may also be necessary to filter ambient air supplied to the patient, for example if the ambient air is likely to contain a virus or bacteria which may be harmful to the patient. It may also be necessary to filter air being exhaled by the patient before it is released to the atmosphere, for example if the patient has a medical condition which may result in a virus or bacteria being exhaled and likely to harm a person nearby.

Generally speaking, in the prior art various different types of masks have been used to address some of the above issues.

Where a patient is to be supplied with pure oxygen, or oxygen mixed with ambient air in a high oxygen/air ratio, a first type of mask is used, as shown in FIG. 1A. As shown in FIG. 1A, the prior art oxygen therapy face mask 10A comprises a face-engaging portion 12A made from a flexible material, a flexible, airtight bag member 36A permanently secured to the face-engaging portion 12A (i.e. the bag member 36A is not meant to be separated from the face-engaging portion 12A). More particularly, the bag member 36A is permanently secured by tape 15A to a neck 14A, which in turn is securely snap fit in a tubular member 16A extending from and integrally formed as part of the face-engaging portion 12A, and is non-removable (i.e. the neck 14A is not intended to be withdrawn from the tubular member 16A and the snap-fit assembly strongly resists removal). A tube attachment member 18A for coupling with a tube (not shown) from an oxygen or oxygen/air source (not shown) extends laterally from the neck 14A and is in fluid communication therewith, and hence is also in fluid communication with the face-engaging portion 12A and the bag member 36A. Fluid communication between the neck 14A and the face-engaging portion 12A is governed by a one-way valve (the location of which is denoted by 20A) carried by the neck 14A, which permits fluid to flow from the neck 14A into the face-engaging portion 12A, but which substantially inhibits fluid flow from the face-engaging portion 12A into the neck 14A. The face-engaging portion 12A includes exhalation ports 22A each comprising a plurality of apertures 23A, which may include diaphragms 24A so that the exhalation ports 22A are one-way valves which inhibit the ingress of ambient air, or may consist solely of the exhalation apertures 23A. In operation, oxygen or an oxygen/air mix is supplied from a tube connected to a pressurized source of oxygen (or oxygen/air mixture), and passes through the tube attachment member 18A into the neck 14A. If the patient is exhaling, the one-way valve at 20A will be closed, and oxygen (or oxygen/air mixture) is forced to travel into the bag member 36A, which inflates. When the patient inhales, a vacuum is created within the face-engaging portion 12A, which draws oxygen (or an oxygen/air mix) from the bag member 36A and/or the tube attachment member 18A through the neck 14A and the one-way valve 20A into the face-engaging portion 12A. When the patient exhales, the one-way valve 20A inhibits the exhaled air from passing into the neck 14A, so the exhaled air escapes through the exhalation ports 22A.

One problem associated with the type of oxygen therapy face mask shown in FIG. 1A where the exhalation ports 22A are one-way valves is that, in the event that the oxygen or oxygen/air supply into the tube attachment member 18A ceases (e.g. because the tank is empty), there is a risk that the patent may suffocate. While known anti-asphyxiation valves may be used to address this issue, this adds cost to the mask, and may have other drawbacks depending on the type of anti-asphyxiation valve used. In practice, this has led to medical staff disabling at least one of the one-way valves governing the exhalation ports 22A, as has been shown in FIG. 1A. While this post-manufacturing modification assists in preventing asphyxiation, it also allows the patient to breathe ambient air instead of the desired oxygen or oxygen/air mix. In addition, this type of mask does not support the periodic administration of inhaled medication.

A second type of mask, shown in FIG. 1B, is used to provide patients with oxygen support in lower concentrations (relative to the amount of oxygen with which the oxygen therapy face mask 10A shown in FIG. 1A is used). This second type of oxygen therapy face mask is shown generally at 10B, and comprises a face-engaging portion 12B, and a neck 14B secured (e.g. by a snap-fit) to the face-engaging portion 12B in fluid communication therewith, with no intervening valve. The neck 14B is securely snap-fit in a tubular member 16B extending from, and integrally formed as part of, the face-engaging portion 12B, and is non-removable (i.e. the neck 14B is not intended to be withdrawn from the tubular member 16B and the snap-fit assembly strongly resists removal). The neck 14B terminates in a tube attachment member 18B in fluid communication with the neck 14B. A plurality of air inlet apertures 21B are defined in the neck 14B, typically arranged about the base of the tube attachment member 18B, and additional exhalation ports 22B, each comprising a plurality of exhalation apertures 23B, are disposed in the sides of the face-engaging portion 12B. The exhalation ports 22A may consist solely of the exhalation apertures 23A, or may include diaphragm members (not shown) so that the exhalation ports 22B operate as one-way valves to inhibit the ingress of ambient air. In operation, where the exhalation ports 22B operate as one-way valves, a patient would inhale ambient air through the air inlet apertures 21B, and oxygen or an oxygen/air mix received from a tube (not shown) attached to the tube attachment member 18B. When the patient exhales, the exhaled air leaves the face-engaging portion primarily through the exhalation apertures 22B, as well as through the air inlet apertures 21B. Where the exhalation apertures 22B consist solely of the exhalation apertures 23B, both inhaled and exhaled air will pass through both the exhalation apertures 23B and the air inlet apertures 21B. Thus, omission or removal of the one-way valves from the exhalation apertures 23B assists in preventing asphyxiation in the event of cessation of oxygen (or oxygen/air mixture) supply from the tube (not shown) to the tube attachment member 18B ceases where the air inlet apertures 22B (which are intended to supplement the flow from the tube) are not large enough to provide enough air for respiration. As with the first type of oxygen therapy mask 10A, this second type of oxygen therapy mask 10B does not support the periodic administration of inhaled medication.

A third type of mask, which is used to support the administration of inhaled medication, is shown in FIG. 1C. The medication administration mask shown in FIG. 1C is denoted generally by the reference numeral 10C, and includes a face-engaging portion 12C and a neck 14C in fluid communication with the face-engaging portion 12C, with no intervening valve. The neck 14C is securely snap-fit in a tubular member 16C extending from, and integrally formed as part of, the face-engaging portion 12C, and is non-removable (i.e. the neck 14C is not intended to be withdrawn from the tubular member 16C and the snap-fit assembly strongly resists removal). The neck 14C is adapted to removably receive a nebulizer 80C, by way of a tubular member 88C extending from the cap 84C of the nebulizer. Specifically, the tubular member 88C is friction fit inside the neck 14C. The nebulizer 80C includes a medication cup 82C which contains a volume of liquid medication and is connected by a tube attachment member (not shown) to a tube 86C coupled to a source of air pressure which cooperates with the internal structure 90C of the nebulizer 80C to atomize the liquid medication for inhalation. The patient can then inhale the medication through the neck 14C. Two large exhalation apertures 23C permit the patient to inhale ambient air, and permit exhaled air to escape the face-engaging portion 12C of the mask. These exhalation apertures also permit the atomized medication to escape into the ambient atmosphere, which is potentially wasteful of expensive medications. In addition, the exhalation apertures also result in undesirable exposure of the health care workers (and others in the immediate environment) to the atomized medication.

A further problem arises when a patient requires more than one type of treatment, such as pure oxygen (or oxygen mixed with ambient air in a high oxygen/ambient air ratio) and inhaled medication, or lower concentrations of oxygen as well as inhaled medication. In such situations, it is necessary to replace the oxygen supply mask, such as the mask 10A or 10B, with a medication supply mask, such as the medication supply mask 10C, in order to administer the medication, and then replace the medication supply mask with the oxygen supply mask. This undermines one of the purposes or benefits of using a mask, namely the isolation of the patient from the ambient atmosphere.

SUMMARY OF THE INVENTION

In one aspect, the present invention is directed to a therapeutic face mask. The therapeutic face mask comprises a face-engaging portion having a fluid aperture, and only a single connector. The connector has a mask-engaging end and a only a single treatment-receiving end, and defines a fluid passageway between the mask-engaging end and the treatment-receiving end. The mask-engaging end of the connector is coupled to the face-engaging portion in fluid communication with the fluid aperture, and the connector has only a single attachment mounting for detachably sealingly receiving a treatment attachment in fluid communication therewith. The attachment mounting is defined at the treatment-receiving end of the connector. The connector has at least one inhalation valve interposed in the fluid passageway between the mask-engaging end and the treatment-receiving end thereof. Each inhalation valve is a one-way valve oriented to permit fluid flow from the treatment-receiving end to the mask-engaging end during inhalation and to inhibit fluid flow from the mask-engaging end to the treatment-receiving end. The therapeutic face mask also includes at least one an anti-asphyxia valve assembly configured to permit fluid flow therethrough from ambient to the face-engaging portion during inhalation only when fluid flow to the treatment-receiving end of the connector is less than inspiratory effort during inhalation. In addition, the therapeutic face mask includes at least one valve-governed exhalation port in fluid communication with the face-engaging portion. Each valve-governed exhalation port is positioned to define an exhalation path from the face-engaging portion to ambient which bypasses the inhalation valve and which permits fluid flow from the face-engaging portion to ambient during exhalation and inhibits fluid flow from ambient to the face engaging portion at least when fluid flow to the treatment-receiving end of the connector exceeds inspiratory effort during inhalation.

In one embodiment, a single exhalation port is defined in a side wall of the connector and is in fluid communication with the face-engaging portion by way of the fluid passageway.

In one embodiment, each exhalation port is defined in the connector and is in fluid communication with the face-engaging portion by way of the fluid passageway, and is positioned between the inhalation valve and the mask-engaging end of the connector. Each exhalation port may have a filter mounting for detachably sealingly receiving a filter assembly.

In one embodiment, each anti-asphyxia valve assembly is associated with a corresponding exhalation port. Each anti-asphyxia valve assembly may comprise a single anti-asphyxia valve disposed in the corresponding exhalation port and oriented to permit fluid flow from the connector to ambient through the exhalation port during exhalation, and to permit fluid flow from ambient to the connector through the exhalation port during inhalation only when fluid flow to the treatment-receiving end of the connector is less than inspiratory effort during inhalation.

In one embodiment, each anti-asphyxia valve comprises an aperture having a single cross member extending thereacross, and a flexible diaphragm secured to the cross member on an outer side of the cross member relative to the fluid passageway.

In another embodiment, the connector includes a valve assembly. In this embodiment, the connector comprises first and second passages, and the valve assembly. The first passage is adjacent the mask-engaging end of the connector, from which first passage fluid can flow into the face-engaging portion and which can also receive fluid from an interior of the face-engaging portion, and the second passage is adjacent the treatment-receiving end of the connector. The valve assembly comprises a single inhalation valve, the exhalation port, and the anti-asphyxia valve assembly. The inhalation valve is associated with the first passage and the second passage, and is operable to permit fluid flow from the second passage to the first passage and inhibit fluid flow from the first passage to the second passage. The exhalation port includes a one-way exhalation valve associated with the first passage and operable to permit fluid flow from the first passage to ambient and to inhibit fluid flow from ambient to the first passage. The anti-asphyxia valve assembly includes a one-way anti-asphyxia valve associated with the first passage and operable to inhibit fluid flow from the first passage to ambient and to permit fluid flow from ambient to the first passage when fluid flow into the second passage is less than inspiratory effort during inhalation. The inhalation valve comprises a disk-like diaphragm located between the first and second passages and movable between open and closed positions, and one of the exhalation valve and the anti-asphyxia valve comprises an annular diaphragm surrounding the disk-like diaphragm of the inhalation valve and movable between open and closed positions. The exhalation port comprises at least one aperture closable by the exhalation valve.

The therapeutic face mask may further comprise an annular filter having a central aperture. The annular filter is positioned in the valve assembly to filter fluid flow from the first passage through the exhalation port to ambient, and permit unfiltered fluid flow from the second passage to the first passage through the central aperture.

A therapeutic face mask according to an aspect of the present invention may further comprise an oxygen reservoir bag detachably secured to the treatment-receiving end of the connector, or a medication supplying nebulizer detachably secured to the treatment-receiving end of the connector.

The present invention is also directed to connectors for therapeutic face masks, as described above.

In another aspect, the present invention is directed to a method of preparing a therapeutic face mask configured for oxygen administration for administration of inhaled medication to a patient while the face-engaging portion is engaged with the patient's face. The method comprises the step of removing from the therapeutic face mask an oxygen reservoir bag that is detachably secured to the therapeutic face mask in fluid communication with a face-engaging portion of the therapeutic face mask, while the face-engaging portion remains engaged with the patient's face and a filter associated with the therapeutic face mask filters air exhaled by the patient. The method also comprises the step of detachably securing a nebulizer to the therapeutic face mask in place of the oxygen reservoir bag so that the nebulizer is in fluid communication with the face-engaging portion of the therapeutic face mask while the face-engaging portion remains engaged with the patient's face and the filter associated with the therapeutic face mask filters air exhaled by the patient.

In still another aspect, the present invention is directed to a method of preparing a therapeutic face mask configured for administration of inhaled medication to a patient for oxygen administration while the face-engaging portion is engaged with the patient's face. The method comprises the step of removing from the therapeutic face mask a nebulizer that is detachably secured to the therapeutic face mask in fluid communication with a face-engaging portion of the therapeutic face mask, while the face-engaging portion remains engaged with the patient's face and a filter associated with the therapeutic face mask filters air exhaled by the patient. The method further comprises the step of detachably securing an oxygen reservoir bag to the therapeutic face mask in place of the nebulizer so that the oxygen reservoir bag is in fluid communication with the face-engaging portion of the therapeutic face mask while the face-engaging portion remains engaged with the patient's face and the filter associated with the therapeutic face mask filters air exhaled by the patient.

The above-described methods may be carried out using the above-described therapeutic face masks.

In another aspect, the present invention is directed to an oxygen reservoir bag. The oxygen reservoir bag comprises a flexible oxygen reservoir bag member, and a valveless neck having a tube attachment member in fluid communication with an interior volume of the neck. The oxygen reservoir bag member is sealingly secured to a lower end portion of the neck so that an interior volume of the oxygen reservoir bag member is in fluid communication with the interior volume of the neck, and the neck is shaped for removable coupling of an open upper end portion thereof to and in fluid communication with a mating connector of a therapeutic face mask.

In still another aspect, the present invention is directed to an oxygen therapy face mask. The oxygen therapy face mask comprises a face-engaging portion having an inlet passage through which oxygen from a pressurized source can be received, and a valve assembly connected to the inlet passage. The valve assembly has a first one-way valve operable to permit flow of oxygen from a source thereof to a patient and inhibit flow in the opposite direction, also has an inlet/outlet passage with a two-way valve permitting ambient air to flow to the patient and permitting exhaled air to flow from the patient to the ambient atmosphere.

In one embodiment, the valve assembly has a first tubular inlet portion to which an oxygen reservoir bag may be detachably connected. The first tubular inlet portion is also capable of detachably receiving, in the absence of the oxygen reservoir bag, a medication supplying nebulizer, whereby medication can be supplied by the nebulizer through the one-way valve into the face-engaging portion for passage to the patient.

In one embodiment, the inlet/outlet passage has a tubular portion connecting the two-way valve with the ambient atmosphere. The tubular portion is capable of detachably receiving a filter assembly operable to filter air passing from the ambient atmosphere to the two-way valve and from the two-way valve to the ambient atmosphere.

In one embodiment, the two-way valve comprises a rod-like support member extending across the inlet/outlet passage and a diaphragm mounted on the support member and having a closed position blocking air flow through the inlet/outlet valve. The diaphragm is bendable by air pressure from either side thereof to enable air to flow through the valve from the higher pressure side of the diaphragm to the lower pressure side thereof.

In a yet further aspect, the present invention is directed to an oxygen reservoir bag. The oxygen reservoir bag comprises a flexible oxygen reservoir bag member, and a neck having an open upper portion end portion and a tube attachment member in fluid communication with an interior volume of the neck. The oxygen reservoir bag member is sealingly secured to a lower end portion of the neck so that an interior volume of the oxygen reservoir bag member is in fluid communication with the interior volume of the neck. A metered dose inhaler port is defined in the neck. The metered dose inhaler port comprises an inner channel defined in the neck in fluid communication with the interior volume of the neck, and an outer channel defined in the neck in fluid communication with ambient. The inner and outer channels are in fluid communication with one another, and the outer channel is larger than the inner channel to define a shoulder between the inner and outer channel. The inner channel is angled toward the oxygen reservoir bag member.

In one embodiment, the neck is valveless and is shaped for removable coupling of the bag to a mating connector of a therapeutic face mask.

In an embodiment, the inner channel and the outer channel are cylindrical and are coaxial with one another, so that the shoulder is an annular shoulder.

DESCRIPTION OF THE DRAWINGS

Embodiments of the invention will now be described, by way of example, with reference to the accompanying drawings, of which.

DESCRIPTION OF PREFERRED EMBODIMENTS

Figure 2:
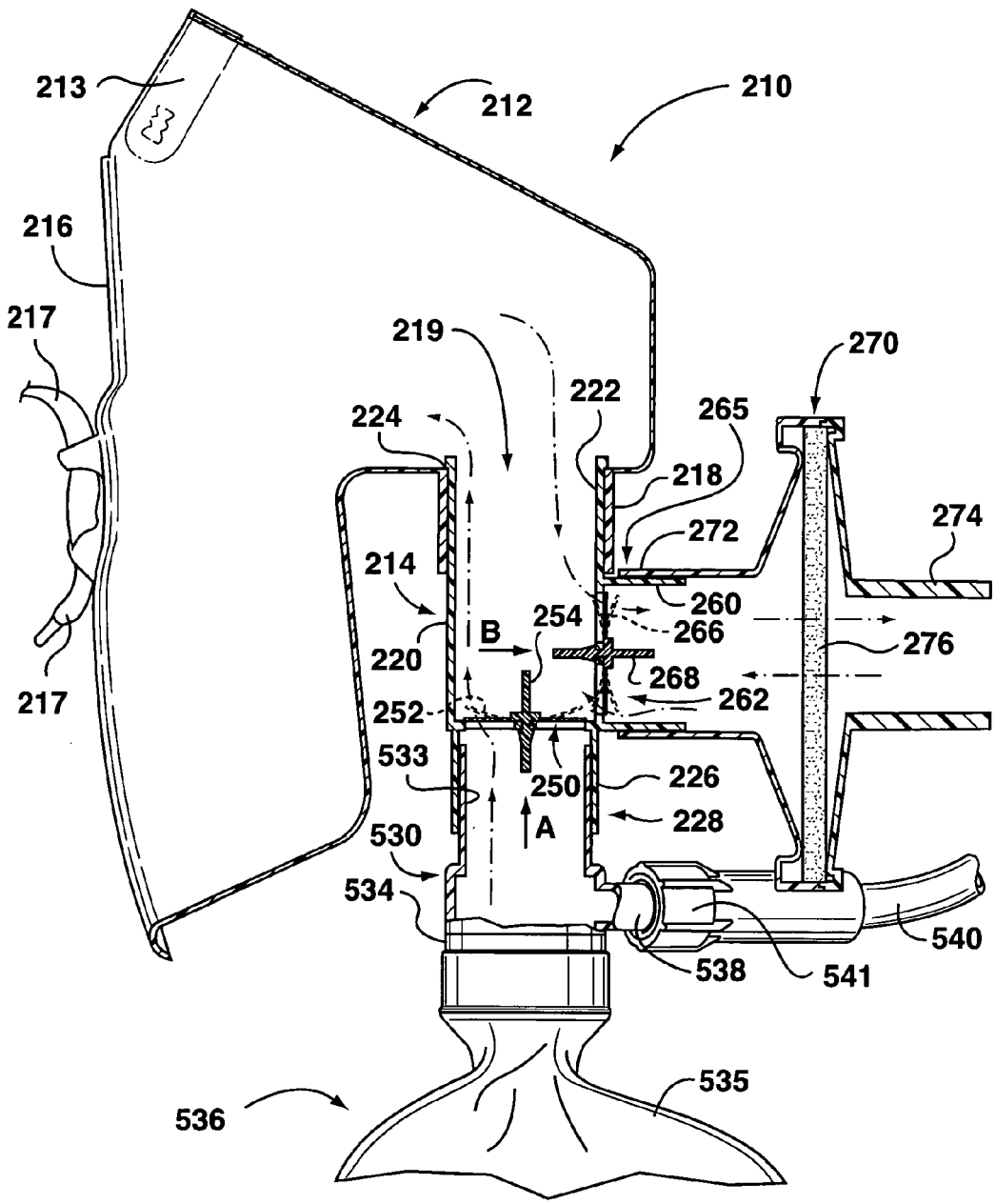
FIG. 2 is a sectional side view, partly in perspective, of a first exemplary therapeutic face mask in accordance with an aspect of the present invention.

Referring to FIG. 2, a therapeutic face mask is indicated generally at 210, and has a face-engaging portion 212 and a connector 214. The face-engaging portion 212 has a peripheral rear edge 216 shaped to engage a patient's face and carrying a pair of attachment straps 217, one of which will encircle the upper portion of a patient's head, above the ears, and the other the lower portion of the patient's head, below the ears. The face-engaging portion is preferably made from a flexible PVC material to enable a good fit with a patient's face. As is known in the art, a bendable nose piece 213, preferably made from aluminum, is secured to the face-engaging portion 212 at the portion thereof which will engage the bridge of the patient's nose, to facilitate a better fit. The face-engaging portion 212 also has a forwardly located, downwardly extending tubular portion 218 defining a fluid aperture 219 through which fluid can enter or leave the face-engaging portion 212. As described below, the connector 214 is received in the tubular portion 218.

The connector 214 has a mask-engaging end 222 and a treatment-receiving end 226, and a main tubular body 220 which in use is substantially vertical and which defines a fluid passageway between the mask-engaging end 222 and the treatment-receiving end 226. The mask-engaging end 222 of the main body portion 220 is a sliding fit in the downwardly extending tubular portion 218 of the face-engaging portion 212, hence, the mask-engaging end 222 of the connector 214 is coupled to the face-engaging portion 212 in fluid communication with the fluid aperture 219. The terminus of the mask-engaging end 222 has an outwardly projecting annular shoulder 224 which snaps into engagement with the upper end of the downwardly extending tubular portion 218 to retain the main tubular body 220 of the connector 214 in engagement with the downwardly extending tubular portion 218. Other suitable attachment techniques, such as adhesive or a friction fit, may also be used without departing from the scope of the present invention.

Figure 5A:
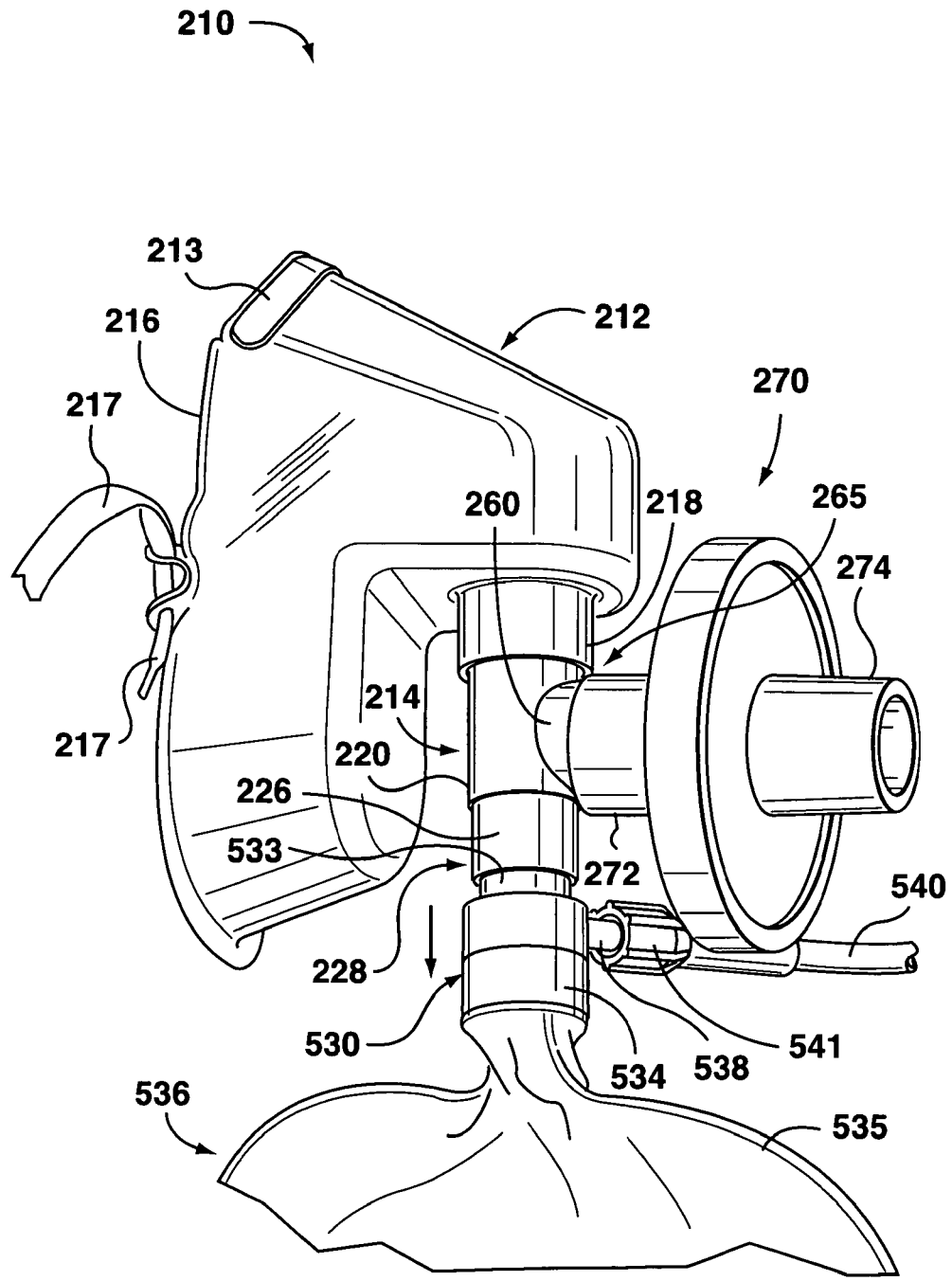
FIG. 5A shows a first exemplary oxygen reservoir bag according to an aspect of the present invention, detachably secured to the therapeutic face mask of FIG. 2.
Figure 5B:
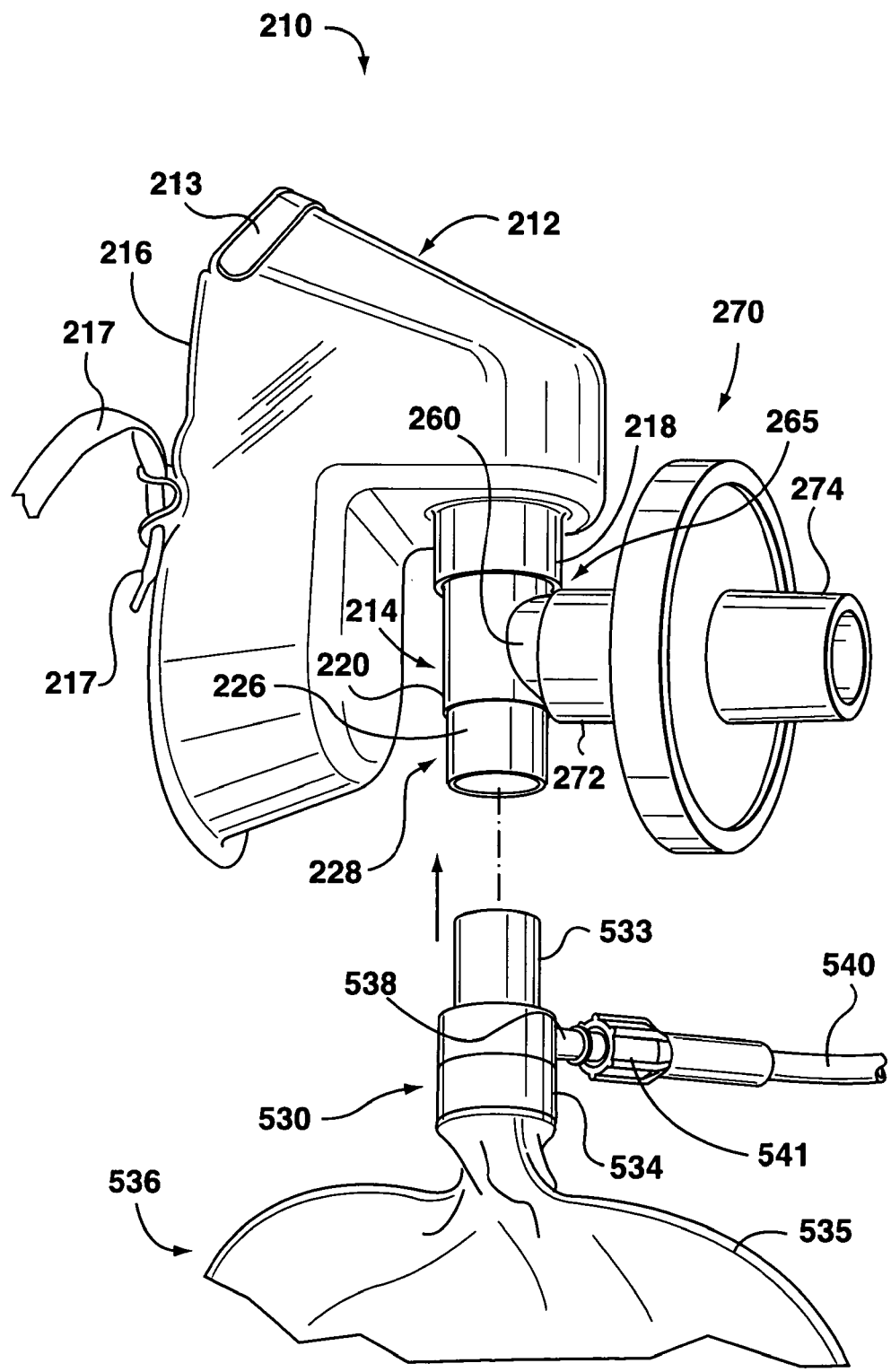
FIG. 5B shows a first exemplary oxygen reservoir bag according to an aspect of the present invention, detached from the therapeutic face mask of FIG. 2.
Figure 6A:
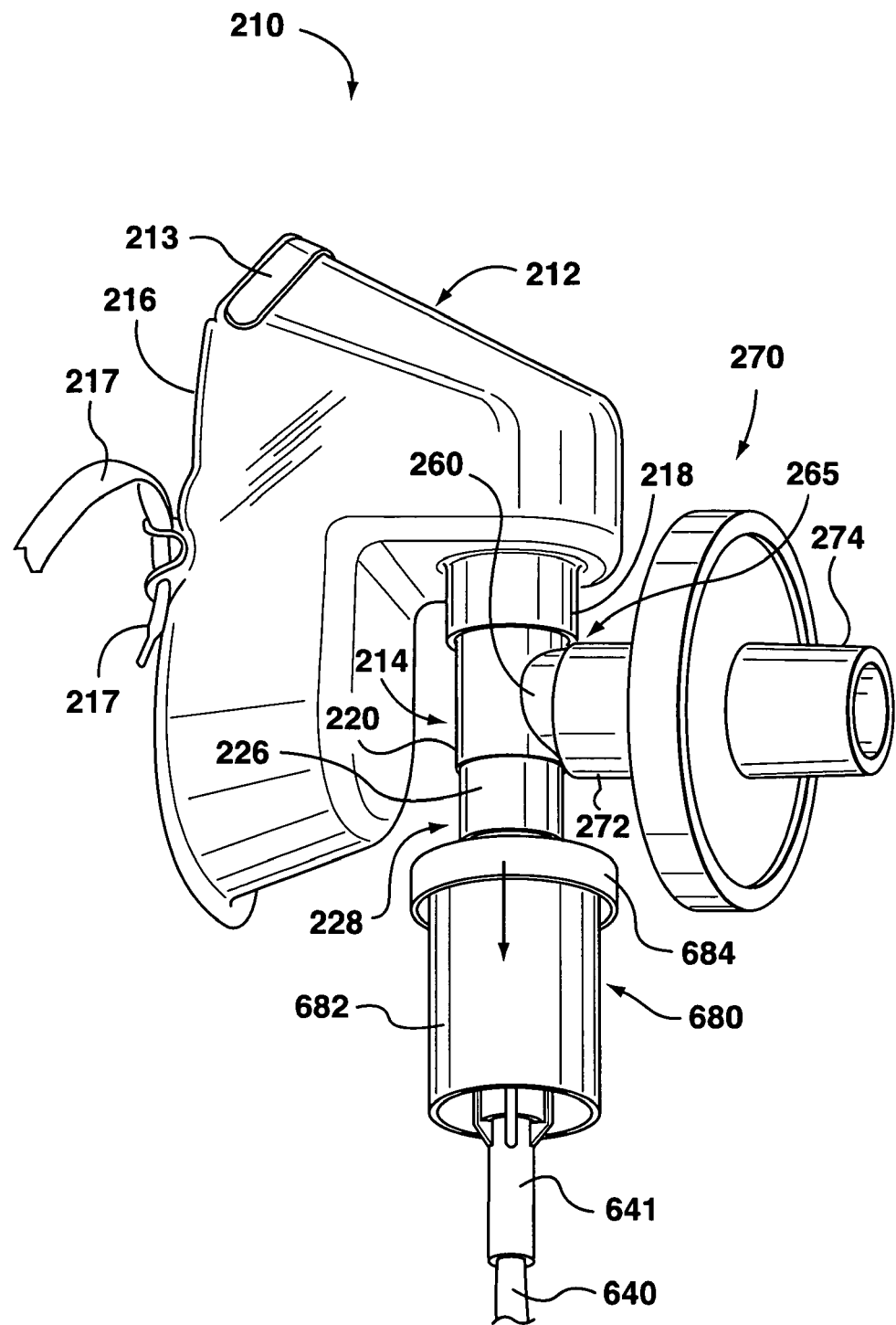
FIG. 6A shows a first exemplary nebulizer according to an aspect of the present invention, detachably secured to the therapeutic face mask of FIG. 2.
Figure 6B:
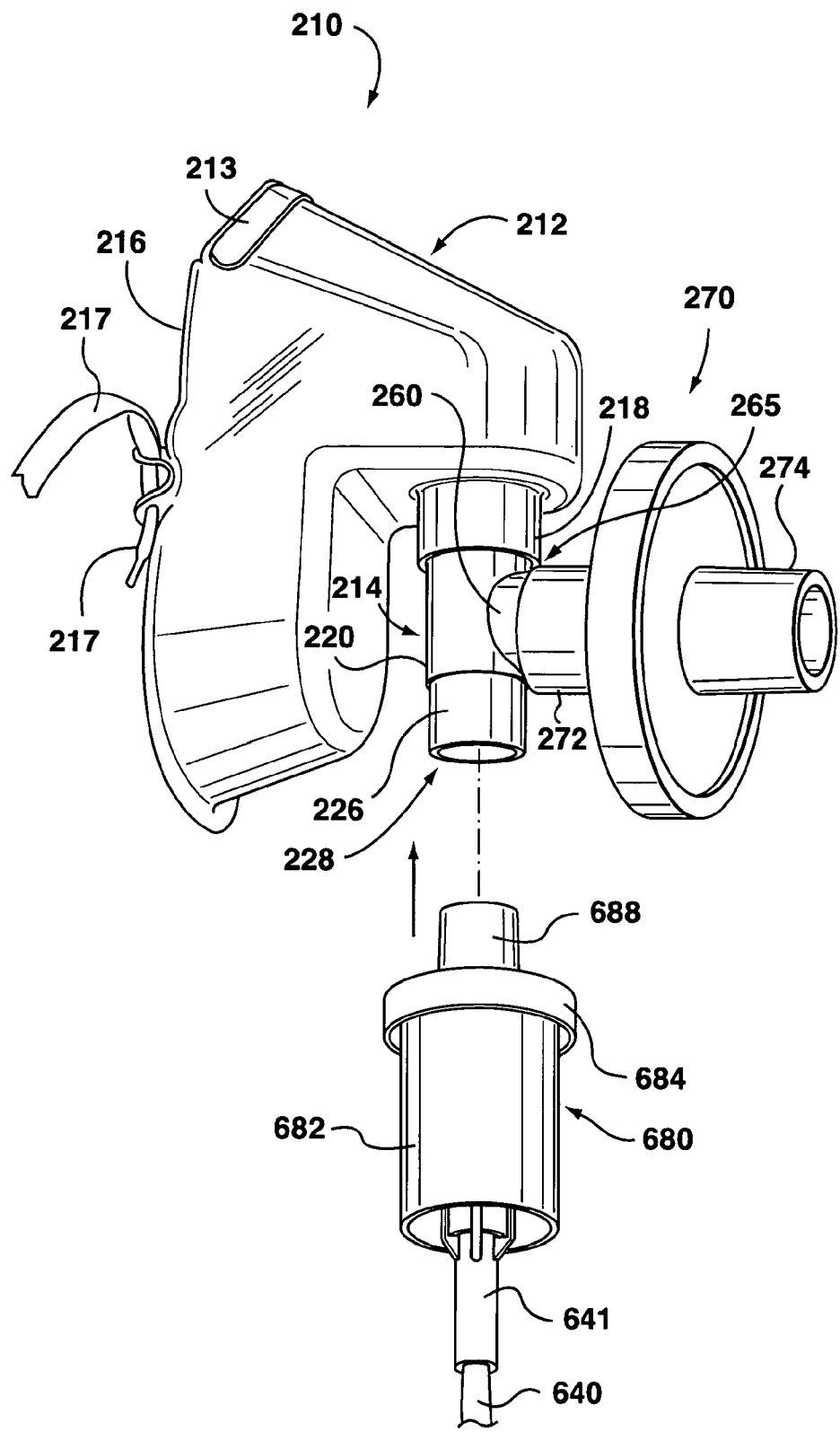
FIG. 6B shows a first exemplary nebulizer according to an aspect of the present invention, detached from the therapeutic face mask of FIG. 2.

The treatment-receiving end 226 of the main tubular body 220 has an attachment mounting for detachably sealingly receiving a mating treatment attachment in fluid communication with the treatment-receiving end 226. In the illustrated embodiment, the attachment mounting is defined by a tubular terminus 228 at the treatment-receiving end 226 which can receive a correspondingly sized tubular neck of a treatment attachment (shown in FIG. 2 as an oxygen reservoir bag 536, described in greater detail in respect of FIGS. 5A and 5B) in a friction fit. When a treatment attachment is so received, a fluid passageway is defined between the treatment attachment and the fluid aperture 219 by way of the main tubular body 220 of the connector 214. Examples of typical treatment attachments include oxygen reservoir bags, as shown in FIGS. 5A and 5B, and nebulizers, as shown in FIGS. 6A and 6B. Various other types of attachment mountings besides the illustrated tubular terminus 228 may also be used, without departing from the scope of the present invention. All that is required is that the attachment mounting be able to detachably sealingly receive a mating treatment attachment. For example, the attachment mounting may be configured to receive both a conventional nebulizer and an oxygen reservoir bag having a correspondingly sized neck.

As shown in FIGS. 5A and 5B, the treatment attachment is an oxygen reservoir bag 536. FIG. 5A shows the oxygen reservoir bag 536 detachably received by the tubular terminus 228 at the treatment-receiving end 226 of the connector 214, and FIG. 5B shows the oxygen reservoir bag 536 detached therefrom. The oxygen reservoir bag 536 includes a neck 530 made from rigid material and a flexible oxygen reservoir bag member 535. The oxygen reservoir bag member 535 is sealingly secured to a lower end portion 534 of the neck 530, for example by tape or adhesive, so that the interior volume of the oxygen reservoir bag member 535 is in fluid communication with the interior volume of the neck 530. The neck 530 includes an open upper end portion 533 having an outer diameter corresponding to the inner diameter of the tubular terminus 228 at the treatment-receiving end 226 of the connector 214. Thus, the neck 530 is shaped, by way of the upper end portion 533, for removable coupling of the oxygen reservoir bag 536 to a mating connector of a therapeutic face mask, namely the connector 214, the treatment-receiving end 226 of which receives the upper end portion 533 in sliding frictional engagement therewith. The neck 530 also has a laterally extending tube attachment member 538 in fluid communication with the neck 530, to which one end 541 of an oxygen supply tube 540 can be detachably connected, the other end of the oxygen supply tube 541 being connected to a source of pressurized oxygen in known manner. It is to be noted that the neck 530 does not carry any valves to govern fluid flow through the neck 530, that is, the neck 530 is valveless. As will be explained below, no valve need be included in the neck 530 because the oxygen reservoir bag 530 is to be used in conjunction with a therapeutic face mask having a connector that includes the requisite valve arrangements.

As shown in FIGS. 6A and 6B, the treatment attachment is a nebulizer. FIG. 6A shows the nebulizer 680 detachably received on the tubular terminus 228 at the treatment-receiving end 226 of the connector 214, and FIG. 6B shows the nebulizer 680 detached therefrom. The nebulizer 680 shown in FIGS. 6A and 6B comprises a medication cup 682 in which a quantity of liquid medication may be disposed, and a removable cap 684. A tube attachment member 686 (FIG. 6B) is adapted to detachably receive one end 641 of an oxygen (or oxygen/air mixture) supply tube 640, and defines a fluid communication path from the supply tube 640 into the medication cup 682. The cap 684 includes an upwardly extending neck 688 (FIG. 6B) which is shaped to enable removable coupling of the nebulizer 680 to a mating connector of a therapeutic face mask, namely the connector 214. In particular, the outer diameter of the upwardly extending neck 688 corresponds to the inner diameter of the tubular terminus 228 at the treatment-receiving end 226 of the connector 214, so that the treatment-receiving end 226 of the connector 214 can receive the upwardly extending neck 688 in a friction fit. Particular details of the operation of the nebulizing or atomizing structure of the nebulizer 680 are outside the scope of the present invention.

As will be explained in greater detail below, because the attachment mounting at the treatment-receiving end 226 of the connector 214 can detachably sealingly receive a treatment attachment, a health care worker can change the treatment attachment without having to remove the therapeutic face mask 210 from the user's face, which, by way of the valve structure and filter attachment to be described shortly, allows the patient to remain isolated during the changeover of treatment attachment.

Figure 3:
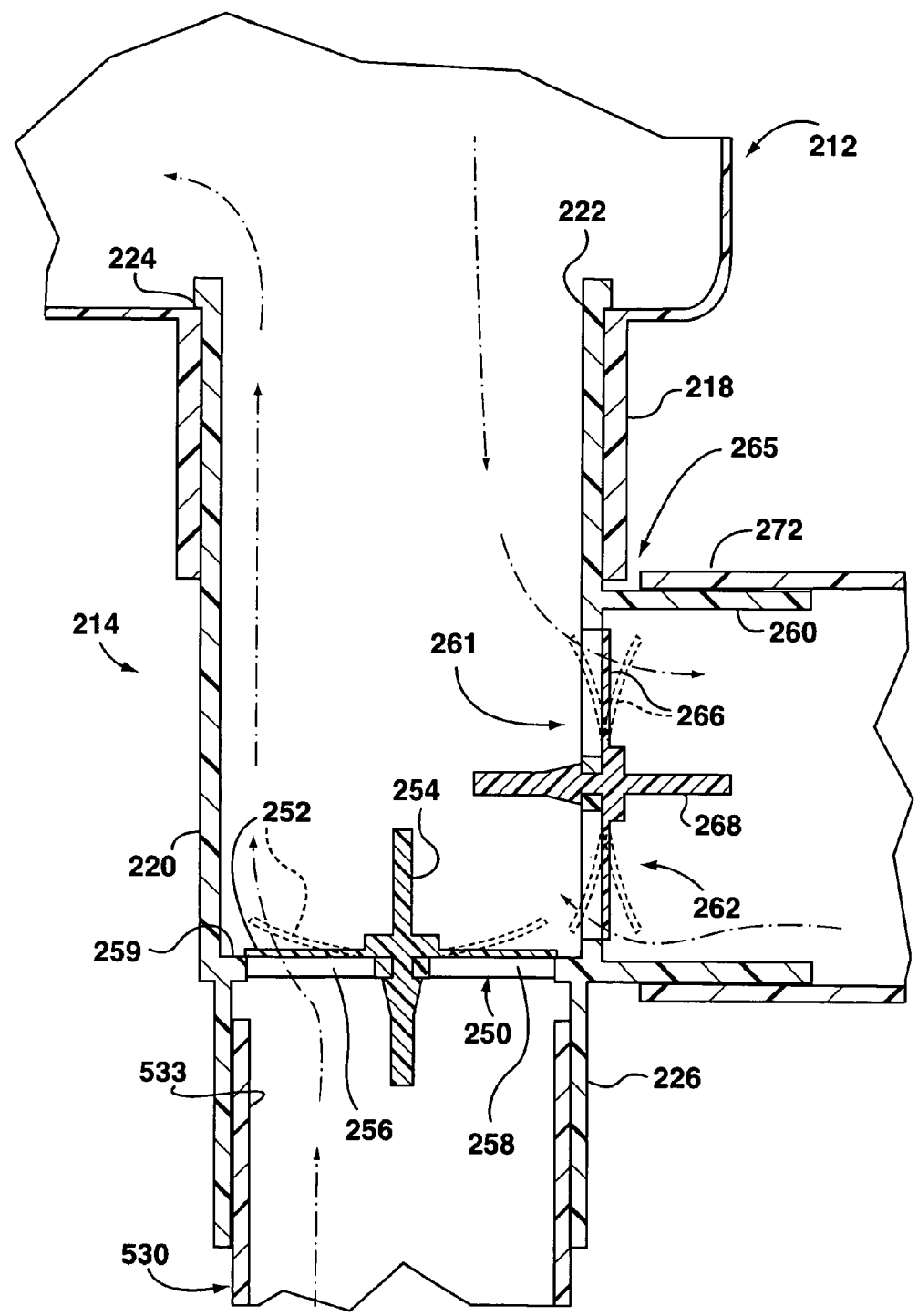
FIG. 3 is an enlarged view of a portion of FIG. 2, showing the one-way and two-way valves with related structure.
Figure 4:
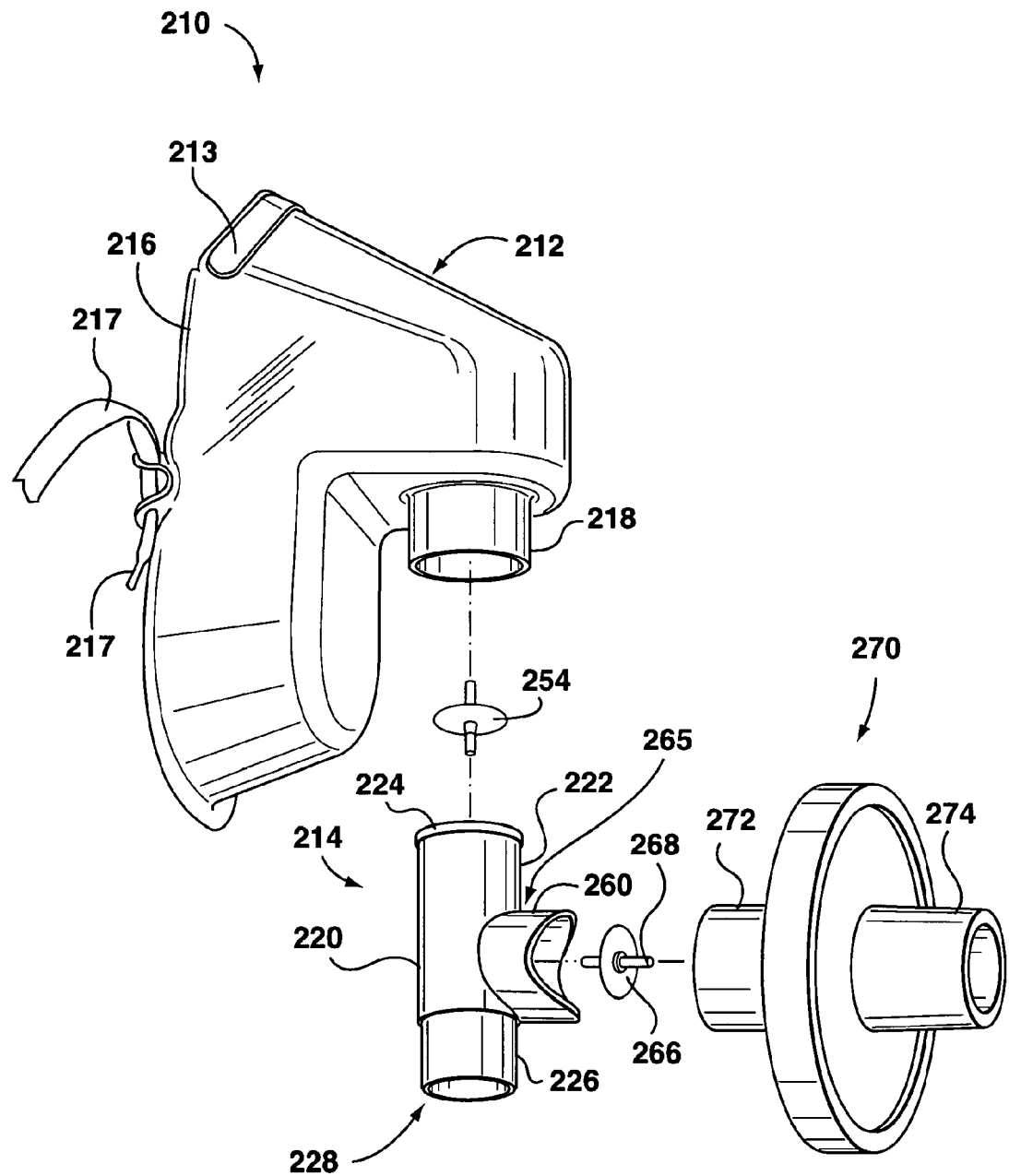
FIG. 4 is an exploded view of the main components of the therapeutic face mask of FIG. 2.

Now referring primarily to FIG. 3, and also to FIG. 2, the connector 214 has an inhalation valve 250 interposed in the main tubular body 220 between the mask-engaging end 222 and the treatment-receiving end 226. The inhalation valve 250 is a one-way valve and is oriented to permit fluid flow from the treatment-receiving end 226 through the mask-engaging end 222 and to inhibit fluid flow from the mask-engaging end 222 through the treatment-receiving end 226. Thus, when the treatment attachment that is attached to the tubular terminus 228 at the treatment-receiving end 226 of the connector 214 is an oxygen reservoir bag, such as the exemplary oxygen reservoir bag 536, oxygen (or an oxygen/air mixture) from the oxygen reservoir bag 536 and the oxygen supply tube 540 can pass through the main tubular body 220 of the connector 214 to the interior of the face-engaging portion 212. Similarly, and as will be explained in greater detail below, when the treatment attachment is a nebulizer, the oxygen (or oxygen/air mixture) containing the atomized medication can also pass through the main tubular body 220 of the connector 214 to the interior of the face-engaging portion 212. In the illustrated embodiment, only a single inhalation valve 250 is shown, it is contemplated that in other embodiments an assembly comprising more than one one-way inhalation valve could be used.

Figure 2A:
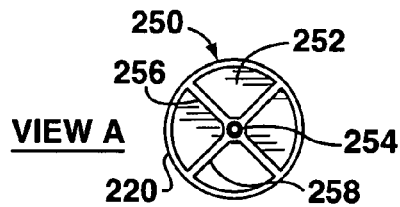
FIG. 2A is a view of a one-way valve of the therapeutic face mask of FIG. 2, taken in the direction of arrow A in FIG. 2.

As best seen in FIG. 2A, in the exemplary connector 214, the inhalation valve 250 comprises a flexible circular diaphragm 252 secured by a retainer 254 at its centre to two substantially mutually perpendicular cross members 256, 258 extending across the main tubular body 220 of the connector. The diaphragm 252 is located on the side of the cross members 256, 258 closest to the mask-engaging end 222 of the connector 214 so that, when the patient inhales, the diaphragm 252 bends upwardly as shown in FIGS. 2 and 3 to permit fluid to flow therethrough from the oxygen reservoir bag 536 and/or supply tube 540, or from the nebulizer 680, into the face-engaging portion 212 and thence to the patient. When the patient is not inhaling, the diaphragm 252 rests against the cross members 256, 258 to inhibit airflow from the face-engaging portion 212 into the treatment-receiving end 226. More particularly, when a patient exhales, the diaphragm 252 is supported by the cross members 256, 258, which helps to prevent bending of the diaphragm 252 under pressure from the exhaled air. Preferably, an annular shoulder 259 is defined adjacent the diaphragm 252 on the side thereof closest to the treatment-receiving end 226 of the connector 14, and the diaphragm 252 is sized so that its circumferential edge rests on and is supported by the annular shoulder 259 when the patient exhales, to provide a more effective seal.

Figure 1A:
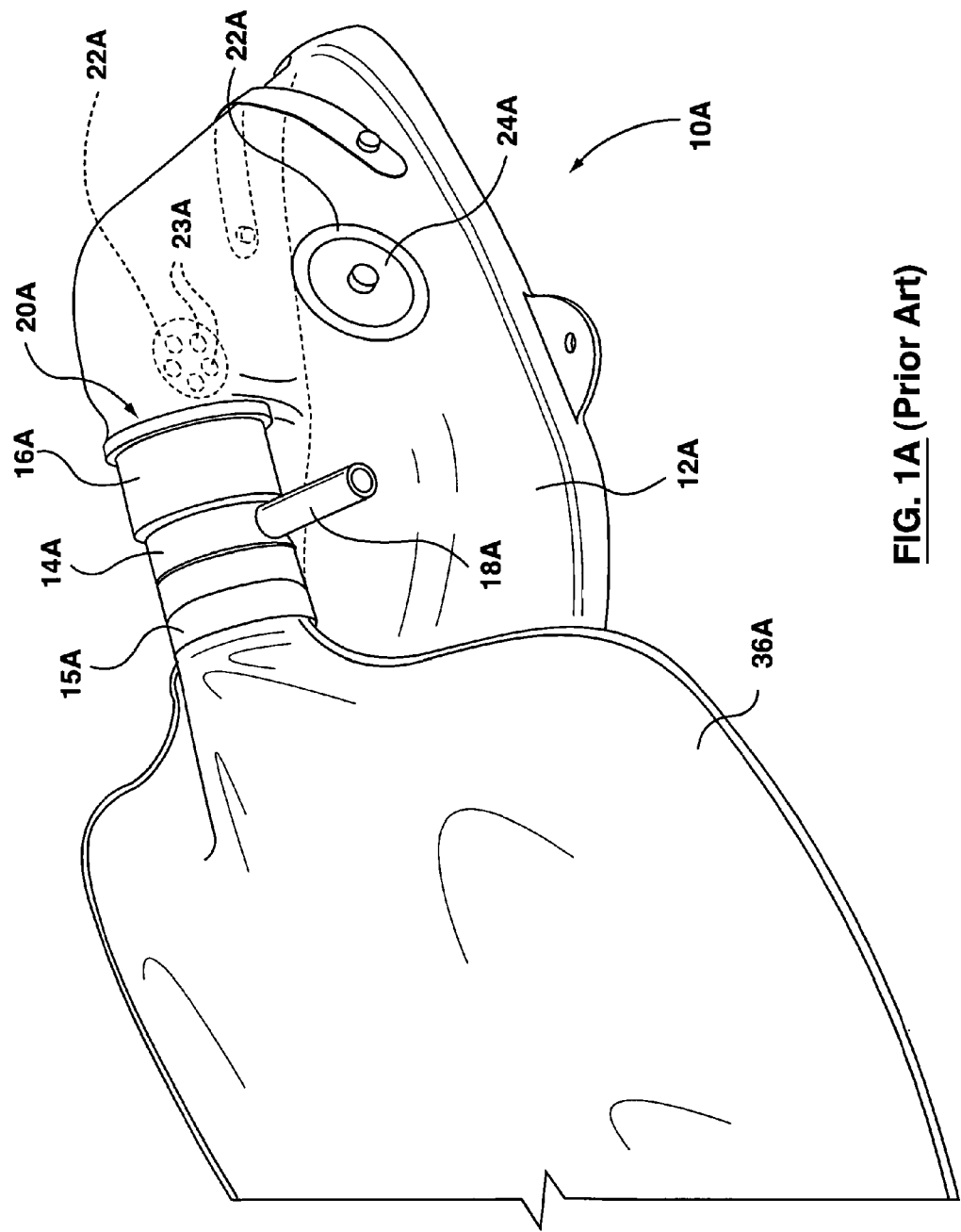
FIG. 1A is a perspective view of a prior art oxygen therapy face mask used to administer pure oxygen or a high oxygen ratio oxygen/air mixture.
Figure 1B:
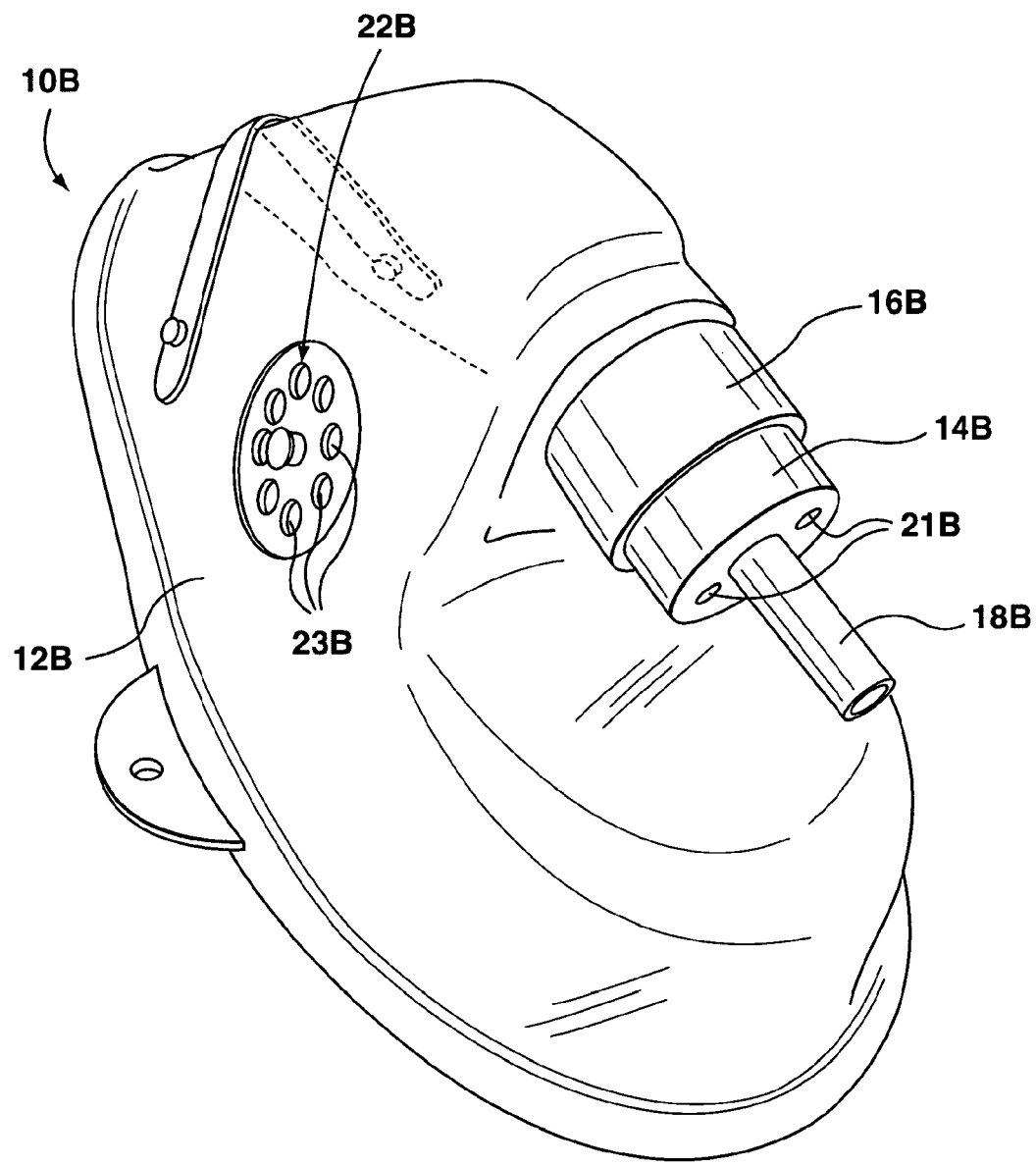
FIG. 1B is a perspective view of a prior art oxygen therapy face mask used to administer an oxygen/air mixture.
Figure 1C:
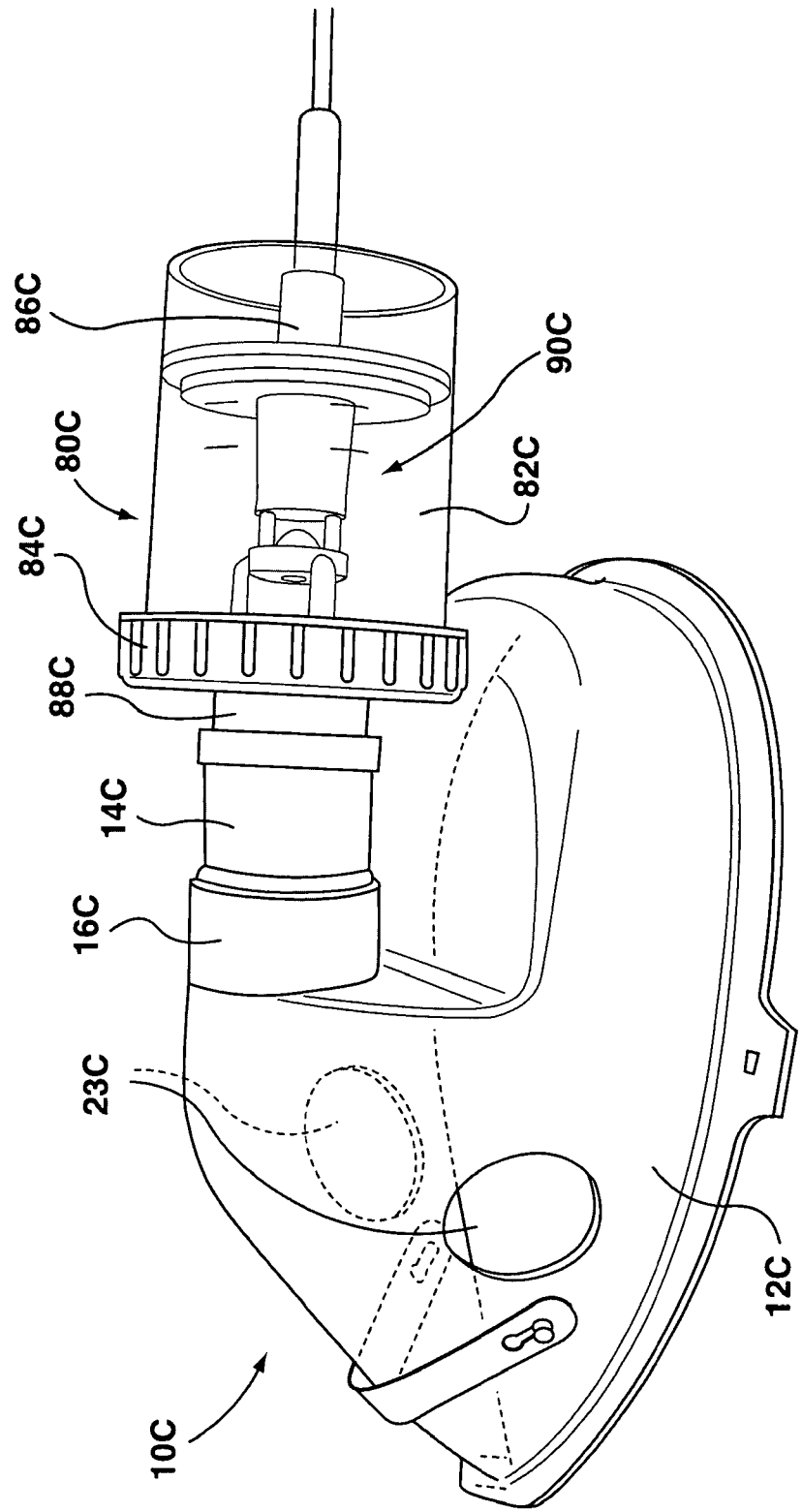
FIG. 1C is a perspective view of a prior art nebulizer face mask used to administer nebulized medication.

The presence of the inhalation valve 250 helps to facilitate effective delivery of medication with a nebulizer, such as the nebulizer 680. Many of the known types of nebulized medication procedures are continuous, in that the flow of oxygen or oxygen/air mixture, and hence of the atomized medication, into the face-engaging portion is continuous. When a conventional nebulizer mask, such as the nebulizer mask 110C illustrated in FIG. 1C, is used, this results in waste of medication during exhalation or coughing, as the medication-laden oxygen or oxygen/air mixture is expelled through the exhalation apertures. This also results in unwanted exposure of the health care worker to medication.

These problems are substantially obviated with the use of a therapeutic face mask according to an aspect of the present invention. When the oxygen reservoir bag 536 is removed and replaced with the nebulizer 680, the inhalation valve 250 acts as a lid because of its measured thickness and relative rigidity. While a patient is exhaling, the inhalation valve 250 is in the closed position, and atomized medication particles contained in the continuous flow of oxygen (or oxygen air/mixture) entering the nebulizer are deflected by the inhalation valve 250 to "rain" back into the nebulizer, rather than entering the face-engaging portion 212, thereby substantially reducing aerosol release to the ambient air during exhalation. The inhalation valve 250 only opens on inhalation to allow the atomized medication particles to enter the face-engaging portion 212 to be supplied to the patient. Thus, the process of medication delivery with a therapeutic face mask in accordance with the present invention is more efficient and significantly reduces undesirable exposure of a care giver to medication.

A therapeutic face mask according to an aspect of the present invention includes at least one exhalation port in fluid communication with the face-engaging portion. The exhalation port should be positioned to define an exhalation path from the face-engaging portion to ambient which bypasses the inhalation valve, so that the inhalation valve (which is a one-way valve) does not obstruct exhalation. In one preferred embodiment, as will be described in greater detail below, an anti-asphyxia valve assembly is associated with the exhalation port. In the illustrated embodiment 210 there is a single exhalation port and associated anti-asphyxia valve assembly, it is contemplated that in other embodiments multiple exhalation ports and associated valve assemblies could be provided.

As best seen in FIG. 3, in the exemplary therapeutic face mask 10, an exhalation port 265 includes an exhalation aperture 261 defined in a side wall of the connector 214, that is, in the main tubular body 220 of the connector 214, and is in fluid communication with the face-engaging portion 212 by way of the fluid passageway defined by the main tubular body 220. Thus, the exhalation port 265 enables communication between the interior of the face-engaging portion 212 and the ambient atmosphere. As can be seen, the exhalation port 265 is positioned between the inhalation valve 250 and the mask-engaging end 222 of the connector 214, and there is thus be defined an exhalation path between the face-engaging portion 212 and ambient which bypasses the inhalation valve 250.

Figure 2B:
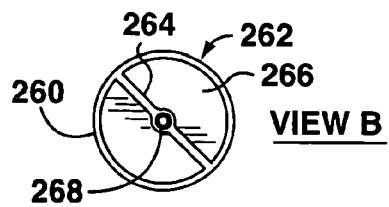
FIG. 2B is a view of a two-way valve of the therapeutic face mask of FIG. 2, taken in the direction of arrow B in FIG. 2.
Figure 2C:
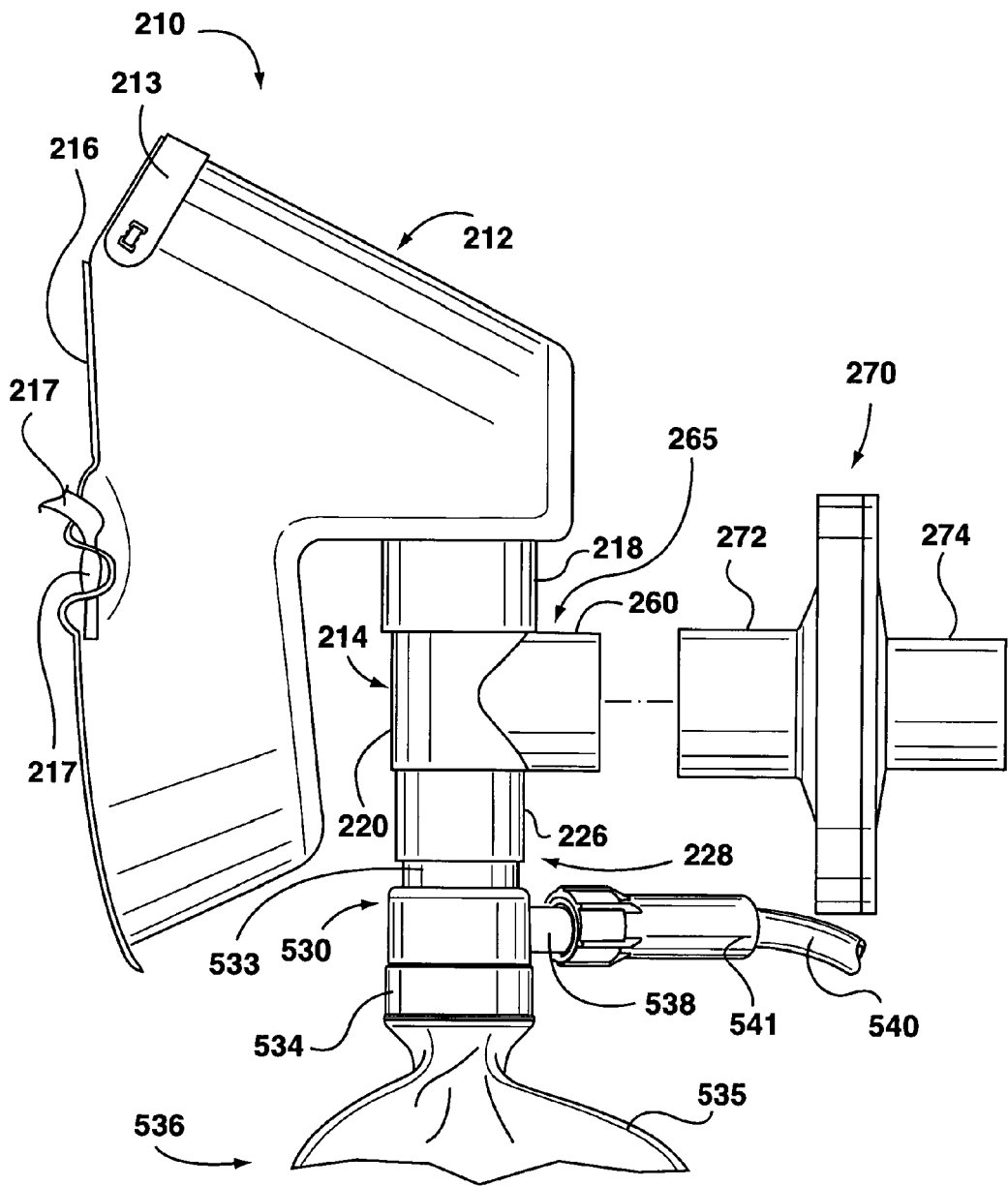
FIG. 2C is a sectional side view, partly in perspective, of the therapeutic face mask of FIG. 2, showing a detachably mountable filter assembly detached therefrom.

The exhalation port 265 also includes a laterally extending tubular outlet portion 260 which surrounds the exhalation aperture 261, and which defines a filter mounting for detachably sealingly receiving a filter assembly. A filter assembly 270 may be detachably connected to the outlet portion 260. More particularly, the filter assembly 270 (best seen in FIG. 2) comprises a tubular body having one tubular end portion 272 slidable over the tubular outlet portion 260 in a friction fit therewith and an outer end portion 274 in communication with the ambient atmosphere. The filter assembly 270 contains a filter 276 to filter air passing into the ambient atmosphere from the exhalation port 265 to the interior of the face-engaging portion 212 and vice-versa (as explained below). FIG. 2C shows the filter assembly 270 detached from the therapeutic face mask 210.

In the exemplary oxygen therapy mask 210, the anti-asphyxia valve assembly is associated with the exhalation port 265 and comprises a single two-way valve 262 disposed in the exhalation port and oriented to permit fluid flow from the connector 214 to ambient through the exhalation port 265, to inhibit fluid flow from ambient to the connector 214 through the exhalation port 265 during inhalation when sufficient fluid is supplied to the treatment-receiving end 226 of the connector, and to permit fluid flow from ambient to the connector 214 through the exhalation port 265 during inhalation when fluid flow to the treatment-receiving end 226 of the connector 214 is less than the inspiratory effort of the patient during inhalation. Thus, the two-way valve 262 governs the exhalation port 265.

The single two-way anti-asphyxia valve 262 is disposed in the tubular outlet portion 260, at the junction between the tubular outlet portion 260 and the main body 220 of the connector 214. As best seen in FIG. 2B, the two-way valve 262 comprises a single cross member 264 extending across the exhalation aperture 261 between opposed sides of the tubular outlet portion 260. A flexible circular diaphragm 266 is secured to the centre of the cross member 264 by a retainer 268, the diaphragm 266 being on the outer side of the cross member 264 relative to the fluid passageway defined by the connector 214. The outer diameter of the diaphragm 266 is preferably equal, with appropriate tolerance, to the inner diameter of the tubular outlet portion 260, so that the circumferential edge of the diaphragm 266 engages the inner surface of the tubular outlet portion 260 to assist in sealing.

Depending on whether oxygen (or an oxygen/air mixture, or an oxygen or oxygen/air mixture containing nebulized medication) is supplied to the treatment-receiving end 226 of the connector 214, inhaling by the patient may cause the two-way valve 262 to open to permit air from the ambient atmosphere to flow therethrough to the interior of the face-engaging portion 212, with the diaphragm 266 bending around the cross member 264. In particular, as long as sufficient oxygen (or oxygen/air mixture, or oxygen or oxygen/air mixture containing nebulized medication) is supplied to the treatment-receiving end 226 of the connector 214, when the patient inhales the inhalation valve 250 will be open, and the inflow of oxygen (or oxygen/air mixture) through the inhalation valve 250 will maintain sufficient pressure in the connector 214 that the diaphragm 266 will not be drawn inward and will substantially seal the exhalation aperture 261, thus inhibiting fluid flow from ambient to the connector 214 through the exhalation port 265 during inhalation. However, if oxygen (or an oxygen/air mixture, or an oxygen or oxygen/air mixture containing nebulized medication) supplied to the treatment-receiving end 226 of the connector 214 is absent or insufficient, such as if the oxygen supply tank is empty, or the oxygen supply tube is obstructed, then inhalation by the patient will generate negative pressure inside the connector 214, which draws the diaphragm 266 inward and causes it to bend around the cross member 264, so that air can flow from ambient through the exhalation aperture 261 into the connector 214 and then into the face-engaging portion 212 so that the patient does not suffocate. Thus, the two-way valve 262 governs the exhalation port 265, and permits fluid flow from the face-engaging portion to ambient (i.e. during exhalation) and inhibits fluid flow from ambient to the face-engaging portion 212 up to the point at which fluid flow to the treatment-receiving end 226 of the connector 214 exceeds the patient's inspiratory effort during inhalation, after which the two-way valve 262 permits fluid flow from ambient to supplement or replace fluid flow to the treatment-receiving end 226 of the connector 214. Thus, the two-way valve 262 is configured to permit fluid flow therethrough from ambient to the face-engaging portion 212 during inhalation only when fluid flow to the treatment-receiving end 226 of the connector 212 is less than inspiratory effort during inhalation. The relative rigidity of the diaphragm 252 of the inhalation valve, and of the diaphragm 266 of the two-way valve 262, should be selected to achieve the aforementioned effect. In a preferred embodiment, the inhalation valve 250 will open at an inspiratory effort of approximately 0.5 cm $H_2O$/l/second, and the two-way valve 262 opens to permit fluid flow from the face-engaging portion 212 to ambient (i.e. exhalation) at approximately 0.75 cm $H_2O$/l/second, and opens to permit fluid flow therethrough from ambient to the face-engaging portion at an inspiratory effort of approximately 1.5 cm $H_2O$/l/second.

When the patient exhales, the inhalation valve 250 remains closed and the two-way valve 262 opens by movement of the diaphragm 266 away from the cross member 264 under pressure from the exhaled air, allowing the exhaled air to escape to ambient.

As noted above, because the attachment mounting can detachably sealingly receive a treatment attachment, the treatment attachment may be changed without removing the therapeutic face mask 210 from the user's face, which, by way of the above-described inhalation valve 250, anti-asphyxia valve 262 and filter assembly 270, allows the patient to remain isolated while the treatment attachment is changed. For example, when medication is to be administered to a patient who had previously been receiving oxygen or an oxygen/air mixture, the oxygen reservoir bag 536 which was attached to the tubular terminus 228 of the connector 214 (FIG. 5A) is removed from the tubular terminus 228 of the connector 214 (FIG. 5B) and is replaced by a medication supplying nebulizer 680, as shown in FIG. 6A. Similarly, when oxygen or an oxygen/air mixture is to be supplied to a patient who had been receiving medication, the medication supplying nebulizer 680 which was attached to the tubular terminus 228 of the connector 214 (FIG. 6A) is removed from the tubular terminus 228 of the connector 214 (FIG. 6B) and is replaced by a oxygen reservoir bag 536, as shown in FIG. 5A.

Thus, according to an aspect of the present invention, an oxygen therapy face mask has a face-engaging portion with an inlet passage through which oxygen from a pressurized source can be received. A valve assembly connected to the inlet passage has a first one-way valve operable to permit flow of oxygen from a source thereof to the patient and prevent flow in the opposite direction, the valve assembly also having an inlet/outlet passage with a two-way valve permitting ambient air to flow to the patient and permitting exhaled air to flow from the patient to the ambient atmosphere.

The valve assembly may have a first tubular inlet portion to which an oxygen reservoir bag may be detachably connected, the first tubular inlet portion also being capable of detachably receiving, in the absence of the oxygen reservoir bag, a medication supplying nebulizer, whereby medication can be supplied by the nebulizer through the one-way valve into the face-engaging portion for passage to the patient.

The inlet/outlet passage may have a tubular portion connecting the two-way valve with the ambient atmosphere, the tubular portion being capable of detachably receiving a filter assembly operable to filter air passing from the ambient atmosphere to the two-way valve and from the two-way valve to the ambient atmosphere.

The two-way valve may comprise a rod-like support member extending across the inlet/outlet passage and a diaphragm mounted on the support member and having a closed position blocking air flow through the inlet/outlet valve, the diaphragm being bendable by air pressure from either side thereof to enable air to flow through the valve from the higher pressure side of the diaphragm to the lower pressure side thereof.

Figure 7:
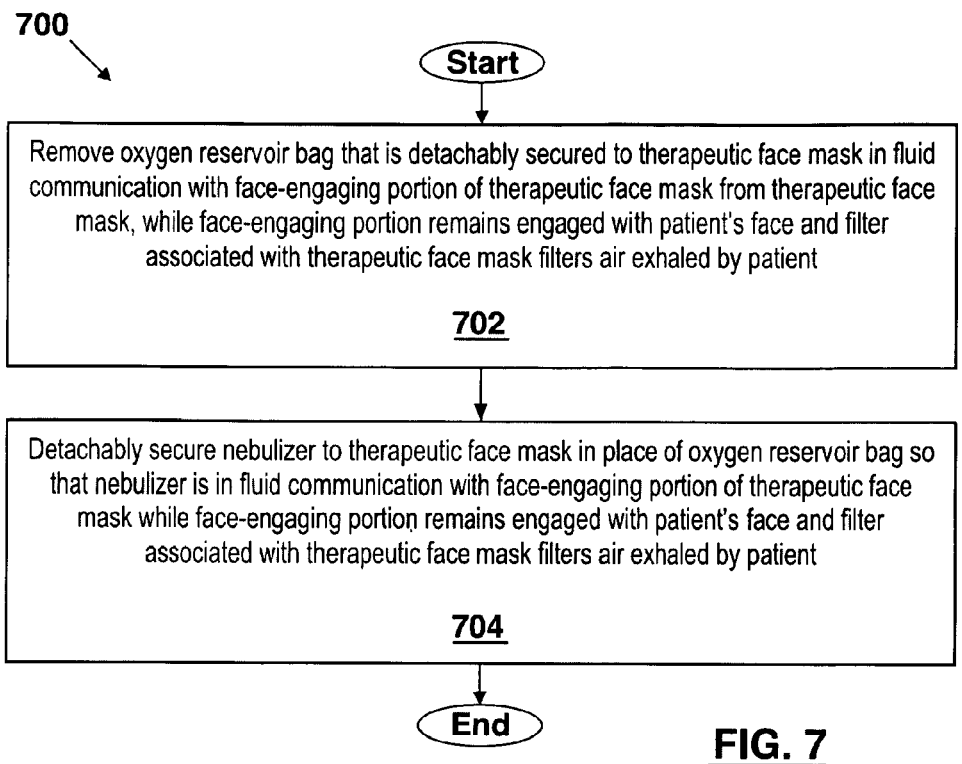
FIG. 7 is a flow chart depicting an exemplary method of preparing a therapeutic face mask that is configured for administration of oxygen to a patient, for administration of inhaled medication to the patient, while the face-engaging portion of the therapeutic face mask is engaged with the patient's face, according to an aspect of the present invention.

Referring now to FIG. 7, an exemplary method of preparing a therapeutic face mask, that is configured for oxygen administration, for administration of inhaled medication to a patient, while the face-engaging portion of the therapeutic face mask is engaged with the patient's face, is shown generally at 700. At step 702, an oxygen reservoir bag that is detachably secured to the therapeutic face mask in fluid communication with a face-engaging portion of the therapeutic face mask is removed from the therapeutic face mask, while the face-engaging portion remains engaged with the patient's face and a filter associated with the therapeutic face mask face filters air exhaled by the patient. At step 704, a nebulizer is detachably secured to the therapeutic face mask in place of the oxygen reservoir bag so that the nebulizer is in fluid communication with the face-engaging portion of the therapeutic face mask while the face-engaging portion remains engaged with the patient's face and a filter associated with the therapeutic face mask face filters air exhaled by the patient. The steps of the method 700 would typically, but not necessarily, be carried out by a health care worker. The method 700 may be carried out, for example, with a therapeutic face mask such as the therapeutic face mask 210, with the oxygen reservoir bag being removed from the treatment-receiving end 226 of the connector 220, and the nebulizer being detachably secured to the treatment-receiving end 226 of the connector 220. As such, the filter employed in the method would be the filter included in the filter assembly 270.

In a similar manner, when oxygen or an oxygen/air mixture is to be administered to a patient who had previously been receiving medication via a nebulizer, the nebulizer attached to the therapeutic face mask (FIG. 6A) is removed from the tubular terminus 228 of the connector 214 (FIG. 6B) and is replaced by the oxygen reservoir bag 536, as shown in FIG. 5A.

Figure 8:
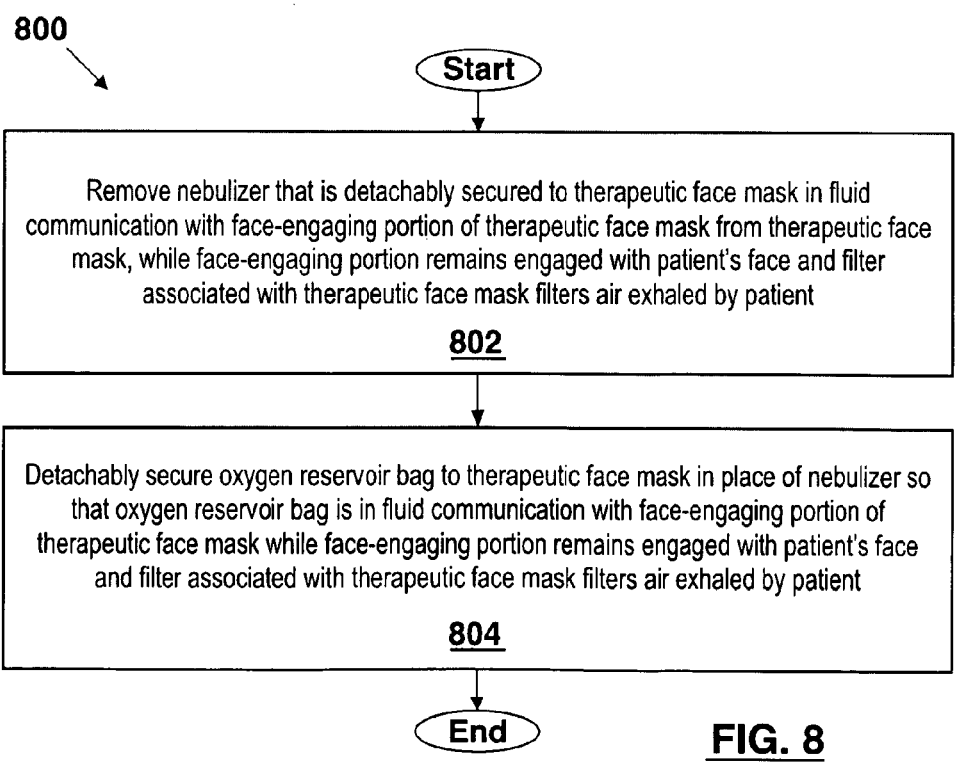
FIG. 8 is a flow chart depicting an exemplary method of preparing a therapeutic face mask, configured for administration of inhaled medication to a patient, for administration of oxygen to the patient, while the face-engaging portion is engaged with the patient's face, according to an aspect of the present invention.

With reference now to FIG. 8, an exemplary method 800 of preparing a therapeutic face mask, configured for administration of inhaled medication to a patient, for oxygen administration, while the face-engaging portion is engaged with the patient's face, is shown. At step 802, a nebulizer that is detachably secured to the therapeutic face mask in fluid communication with a face-engaging portion of the therapeutic face mask is removed from the therapeutic face mask, while the face-engaging portion remains engaged with the patient's face and a filter associated with the therapeutic face mask face filters air exhaled by the patient. At step 804, an oxygen reservoir bag is detachably secured to the therapeutic face mask in place of the nebulizer so that the oxygen reservoir bag is in fluid communication with the face-engaging portion of the therapeutic face mask while the face-engaging portion remains engaged with the patient's face and a filter associated with the therapeutic face mask face filters air exhaled by the patient. As with the method 700, the steps of the method 800 may be carried out by a health care worker, and the method 800 may be carried out, for example, with a therapeutic face mask such as the therapeutic face mask 210, with the nebulizer 680 being removed from the treatment-receiving end 226 of the connector 214, and the oxygen reservoir bag 536 being detachably secured to the treatment-receiving end 226 of the connector 214.

Other types of masks may be modified in accordance with aspects of the present invention to enable selective removable attachment of a treatment attachment, such as a nebulizer and an oxygen reservoir bag. For example, a therapeutic face mask having certain structural features similar to those of the oxygen therapy face mask disclosed in U.S. Pat. No. 7,360,538 may be modified and adapted in accordance with aspects of the present invention. U.S. Pat. No. 7,360,538 is hereby incorporated by reference in its entirety.

Figure 9:
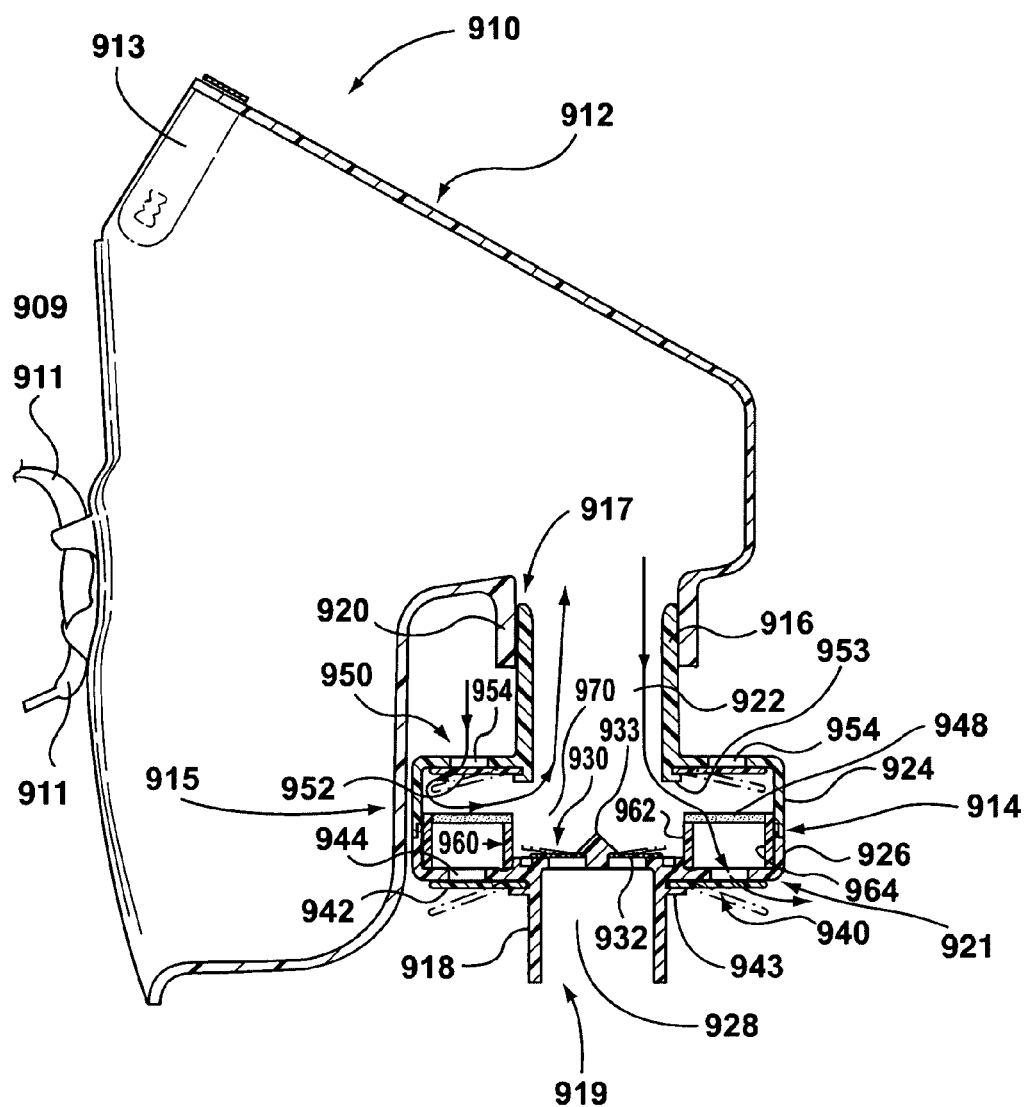
FIG. 9 is a sectional view of a second exemplary therapeutic face mask in accordance with an aspect of the present invention.
Figure 10:
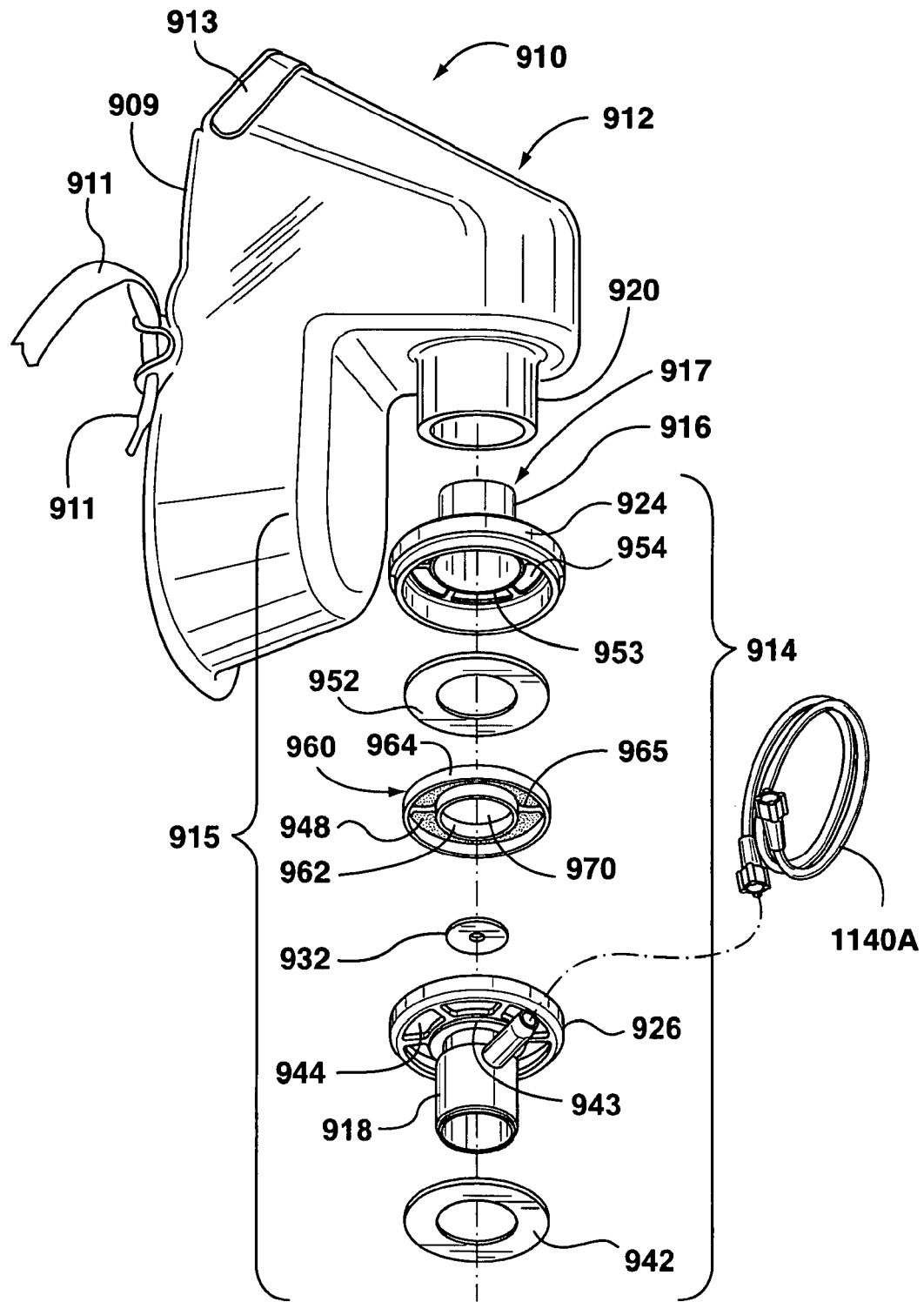
FIG. 10 is an exploded view the main components of the therapeutic face mask of FIG. 9.

Referring now to FIGS. 9 and 10, a therapeutic face mask having certain structural features similar to those described and depicted in U.S. Pat. No. 7,360,538, and adapted in accordance with aspects of the present invention, is now described. This therapeutic face mask is denoted generally by the reference numeral 910. The therapeutic face mask 910 has a face-engaging portion 912 and a connector 914 connected thereto, with the connector 914 including a valve assembly 915. As with the therapeutic face mask 210, the face-engaging portion 912 has a peripheral rear edge 909 shaped to engage a patient's face and carrying a pair of attachment straps 911, one of which will encircle the upper portion of a patient's head, above the ears, and the other the lower portion of the patient's head, below the ears, and a bendable nose piece 913.

The connector 914 comprises an upper tubular body portion 916 and a lower tubular body portion 918 connected to each other. The upper tubular body portion 916 has its upper end portion 917, that is, its mask-engaging end 917, inserted into a downwardly extending tubular portion 920 which defines a fluid aperture of the face-engaging portion 912, thus, the mask-engaging end 917 of the connector 914 is coupled to the face-engaging portion 912 in fluid communication with the fluid aperture thereof The upper tubular body portion 916 may be secured within the downwardly extending tubular portion 920 of the face-engaging portion 912 by way of a friction fit, adhesive, or may be modified to include an outwardly projecting annular shoulder (not shown), similar to the outwardly projecting annular shoulder 224 of the therapeutic face mask 10, which snaps into engagement with a corresponding annular shoulder (not shown) at the upper end of the downwardly extending tubular portion 920.

The upper tubular body portion 916 provides a first passage 922 adjacent the mask-engaging end 917 of the connector 914, from which first passage 922 fluid can flow into the face-engaging portion 912 and which can also receive fluid from the interior of the face-engaging portion 912. The lower end portion 924 of the upper tubular body portion 916 is enlarged, as also is the upper end portion 926 of the lower tubular body portion 918. The enlarged upper end portion 926 of the lower tubular body portion 918 is secured to the enlarged lower end portion 924 of the upper tubular body portion 916. The lower tubular body portion 918 provides a second passage 928 adjacent the treatment-receiving end 919 of the connector 914. The treatment-receiving end 919 of the connector 914 has an attachment mounting for detachably sealingly receiving a treatment attachment in fluid communication therewith. In the illustrated embodiment, the attachment mounting is defined by the tubular shape of the treatment-receiving end 919 of the connector 914, which can receive a correspondingly sized tubular neck of a treatment attachment in a friction fit to define a fluid passageway, by way of the connector 914, between the treatment attachment and the downwardly extending tubular portion 920 defining the fluid aperture of the face-engaging portion 912.

The connector 914 includes a valve assembly 915 which is disposed within, and includes portions of, the enlarged upper end portion 926 of the lower tubular body portion 918 and the enlarged lower end portion 924 of the upper tubular body portion 916.

The valve assembly 915 includes an inhalation valve 930, which is a one-way valve 930, and is associated with the first passage 922 and the second passage 928. Specifically, the inhalation valve 930 is provided at the junction of the first and second passages 922, 928 and is therefore interposed in the fluid passageway defined by the connector 914 between the mask-engaging end 917 and the treatment-receiving end 919 thereof. The inhalation valve 930 is operable to permit fluid flow from the second passage 928 to the first passage 922 during inhalation and inhibit fluid flow from the first passage 922 to the second passage 928, and thus is oriented to permit fluid flow from the treatment-receiving end 919 through the mask-engaging end 917 and to inhibit fluid flow from the mask-engaging end 917 through the treatment-receiving end 919. In the illustrated embodiment, the inhalation valve 930 comprises a disk-like diaphragm 932 at the upper end of the second passage 928. The disk-like diaphragm 932 is retained in position by a central headed pin 933 carried by the lower tubular body portion 918, and is movable between open and closed positions. Normally, the diaphragm 932 is in the closed position and closes the upper end of the second passage 928 and remains closed when the patient exhales, but a sufficiently lower pressure in the first passage 922 relative to the pressure in the second passage 928, such as would be caused by a patient inhaling, causes the diaphragm 932 to move upwardly into the open position and permit fluid to flow from the second passage 928 into the first passage 922 and hence into the face-engaging portion 912. Preferably, the inhalation valve 930 will open when the patient exerts an inspiratory effort of approximately 1.0 cm $H_2O$/l/second. In the illustrated embodiment, only a single inhalation valve 930 is shown, it is contemplated that in other embodiments an assembly comprising more than one one-way inhalation valve could be used.

The valve assembly 915 also includes an exhalation port 921 defined in the connector 914 and which is in fluid communication with the face-engaging portion 912 by way of the fluid passageway defined by the connector 914. The exhalation port 921 includes a one-way exhalation valve 940, which is operable to permit fluid flow from the first passage 922 to the external atmosphere and to inhibit fluid flow from the external atmosphere to the first passage 922. As can be seen, the exhalation port 921 is positioned to define an exhalation path between the face-engaging portion 912 and ambient which bypasses the inhalation valve 930. The exhalation valve 940 comprises an annular diaphragm 942 which surrounds the disk-like diaphragm 932 of the inhalation valve 930 and is retained by an annular lip 943 on the lower end of the upper end portion 926 of the lower tubular body portion 918. The exhalation port 921 also includes one or more exhalation apertures 944 defined in the lower part of the enlarged upper portion 926 of the lower tubular body portion 918. Thus, the exhalation valve 940 is associated with the first passage 922. The exhalation apertures 944 are normally closed by the annular diaphragm 942, and the exhalation valve 940 preferably opens (i.e. the annular diaphragm 942 bends away from the exhalation apertures 944 to permit fluid flow therethrough) at approximately 1.2 cm $H_2O$/l/second and the patient can exhale normally. Accordingly, the exhalation valve 940 governs the exhalation port 921, and which permits fluid flow from the face-engaging portion to ambient during exhalation. The exhalation valve 940 also inhibits fluid flow from ambient to the face-engaging portion 912 not only when fluid flow to the treatment-receiving end 919 of the connector 914 exceeds inspiratory effort during inhalation, but also when such fluid flow is equal to or less than inspiratory effort during inhalation. When fluid flow to the treatment-receiving end 919 of the connector 914 is less than inspiratory effort during inhalation, the anti-asphyxia valve assembly described below will assist in preventing asphyxiation. In the illustrated embodiment, a single exhalation valve 940 is provided, in other embodiments, multiple exhalation valves may be used.

Optionally, an annular filter 948 having a central aperture 970 is disposed in the valve assembly 915 to filter air exhaled by a patient. Specifically, the annular filter 948 is positioned in the valve assembly 915 to filter fluid flow from the first passage 922 through the exhalation port 921 to ambient, and to permit unfiltered fluid flow from the second passage 928 to the first passage 922 through its central aperture 970.

In the illustrated embodiment, the annular filter 948 is carried by an annular filter support 960 comprising radially spaced inner and outer cylindrical walls 962, 964, respectively. The inner cylindrical wall 962 is connected to the outer cylindrical wall 964 by a plurality of radially extending spokes 966 which define a plurality of apertures 968 (see FIG. 10) therebetween, and which also support the annular filter 948. The edges of the inner and outer cylindrical walls 962, 964 opposite the spokes 966 are secured in fluid-tight, sealing engagement with the base of the enlarged upper end portion 926 of the lower tubular body portion 918, with the annular filter support 960 and hence the annular filter member 948 generally surrounding the inhalation valve 930, so that the central aperture 970 defined by the annular filter support 960 and the annular filter 948 is generally aligned with the inhalation valve 930. Accordingly, fluid entering the connector 914 via the second passage 928 and passing through the inhalation valve 930 is able to pass through the central aperture 970 to the first passage 922 without being filtered. Thus, when the treatment attachment is a nebulizer, the atomized medication will not be filtered out of the fluid before reaching the patient. When a patient exhales, the exhaled air is inhibited from travelling from the first passage 922 to the second passage 928 by the one-way inhalation valve 930, and the inner cylindrical wall 962 prevents the exhaled air from reaching the exhalation valve 940 without passing through the annular filter 948. In an alternate embodiment (not shown), an annular filter may surround the inhalation valve 930 at the base of the enlarged upper end portion 926 to cover the exhalation apertures 944, so that exhaled air passing through the exhalation apertures 944 must also pass through the annular filter while incoming oxygen (or an oxygen/air mixture, or a medication-laden oxygen/air mixture) passes through the central aperture of the annular filter and therefore is not filtered.

The valve assembly 915 further comprises an anti-asphyxia valve assembly which includes a one-way anti-asphyxia valve 950. As will be explained in greater detail below, the anti-asphyxia valve 950 is operable to permit fluid flow from the external atmosphere to the first passage 922 when fluid flow into the second passage 928 is less than inspiratory effort of the patient during inhalation, and to inhibit fluid flow from the first passage 922 to the external atmosphere. The anti-asphyxia valve 950 comprises an annular diaphragm 952 retained at the top of the enlarged lower end portion 926 of the upper tubular body portion 916 by an annular lip 953. Thus, the anti-asphyxia valve 950 is associated with the first passage 922. The annular diaphragm 952 normally closes one or more anti-asphyxia apertures 954 in the enlarged lower end portion 924 of the upper tubular body portion 916 to isolate the first passageway 922 from the external atmosphere. The construction of the inhalation valve 930 and the anti-asphyxia valve 950 is such that the anti-asphyxia valve 950 normally remains closed when oxygen (or an oxygen/air mixture or medication-laden oxygen air mixture) is being inhaled by a patient after passage through the inhalation valve 930. In a preferred embodiment, this is achieved by a valve construction in which the inhalation valve 930 opens when the patient exerts an inspiratory effort of a approximately 1.0 cm $H_2O/l/$ second (as noted above) and the anti-asphyxia valve 950 opens (i.e. the annular diaphragm 952 bends away from the anti-asphyxia apertures 954 to permit fluid flow therethrough) at an inspiratory effort of approximately 1.3 cm $H_2O/l/$second. Thus, the anti-asphyxia valve 950 opens to permit fluid flow therethrough from ambient to the face-engaging portion 912 during inhalation only when fluid flow to the treatment-receiving end 919 of the connector 914 is less than inspiratory effort during inhalation. In the illustrated embodiment, a single anti-asphyxia valve 950 is provided, in other embodiments, multiple anti-asphyxia valves may be used.

As indicated above, the tubular shape of the treatment-receiving end 919 of the connector 914 defines an attachment mounting which can receive a correspondingly sized tubular neck of a treatment attachment in a friction fit. Examples of suitable attachment mountings include oxygen reservoir bags, and nebulizers.

Figure 11A:
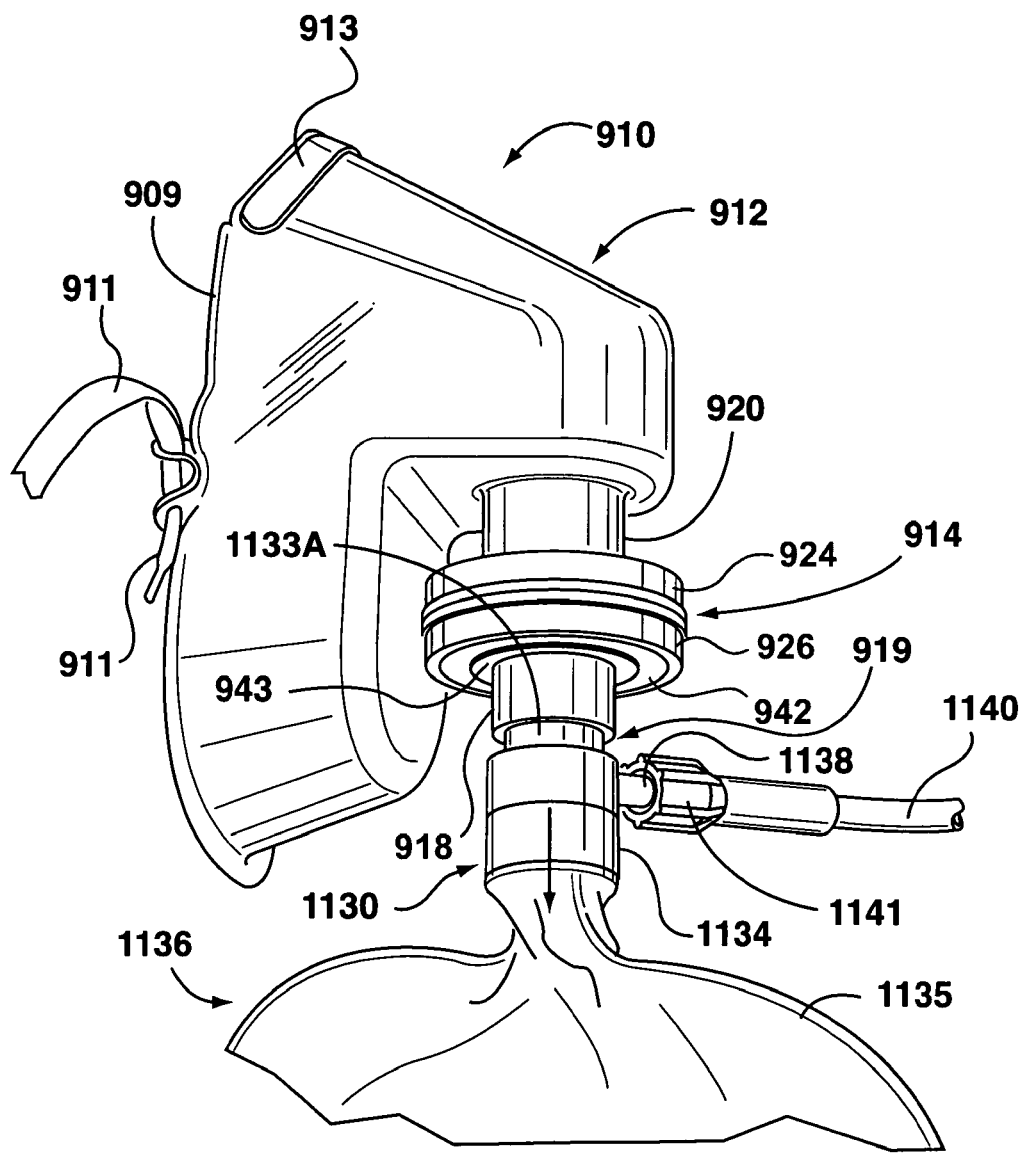
FIG. 11A shows a second exemplary oxygen reservoir bag according to an aspect of the present invention, detachably secured to the therapeutic face mask of FIG. 9.
Figure 11B:
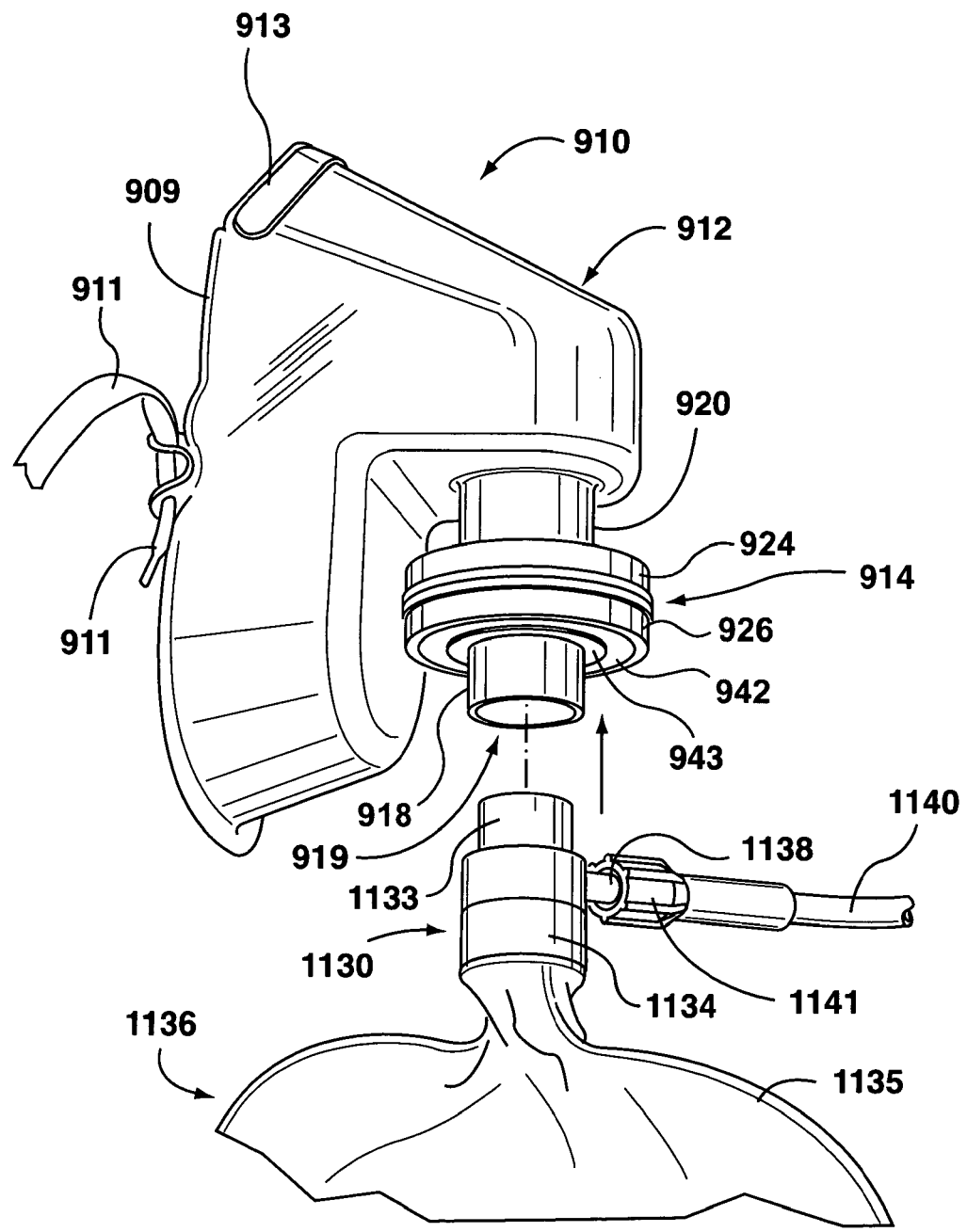
FIG. 11B shows a second exemplary oxygen reservoir bag according to an aspect of the present invention, detached from the therapeutic face mask of FIG. 9.

As shown in FIGS. 11A and 11B, the treatment attachment is an oxygen reservoir bag 1136. FIG. 11A shows an oxygen reservoir bag 1136 detachably mounted on the treatment-receiving end 919 of the connector 914, and FIG. 11B shows oxygen reservoir bag 1136 detached therefrom. The oxygen reservoir bag 1136 includes a neck 1130 made from rigid material and a flexible oxygen reservoir bag member 1135. The oxygen reservoir bag member 1135 is sealingly secured to a lower end portion 1134 of the neck 1130, and the neck 1130 includes an open upper end portion 1133 whose outer diameter corresponds to the inner diameter of the lower tubular body portion 918 at the treatment-receiving end 919 of the connector 914. Thus, the neck 1130 is shaped, by way of the upper end portion 1133, to enable the oxygen reservoir bag 1136 to be removably secured to a mating connector of a therapeutic face mask, in this case the lower tubular body portion 918 defining the treatment-receiving end 919 of the connector 914, which can receive the upper end portion 1133 in a friction fit. A tube attachment member 1138 extends laterally from the neck 1130 in fluid communication therewith, for detachably receiving one end 1141 of an oxygen supply tube 1140. As with the oxygen reservoir bag 536, the neck 1130 is valveless; there is no need to include a valve in the neck 1130 because of the valve assembly 915 included in the therapeutic face mask 910.

Figure 12A:
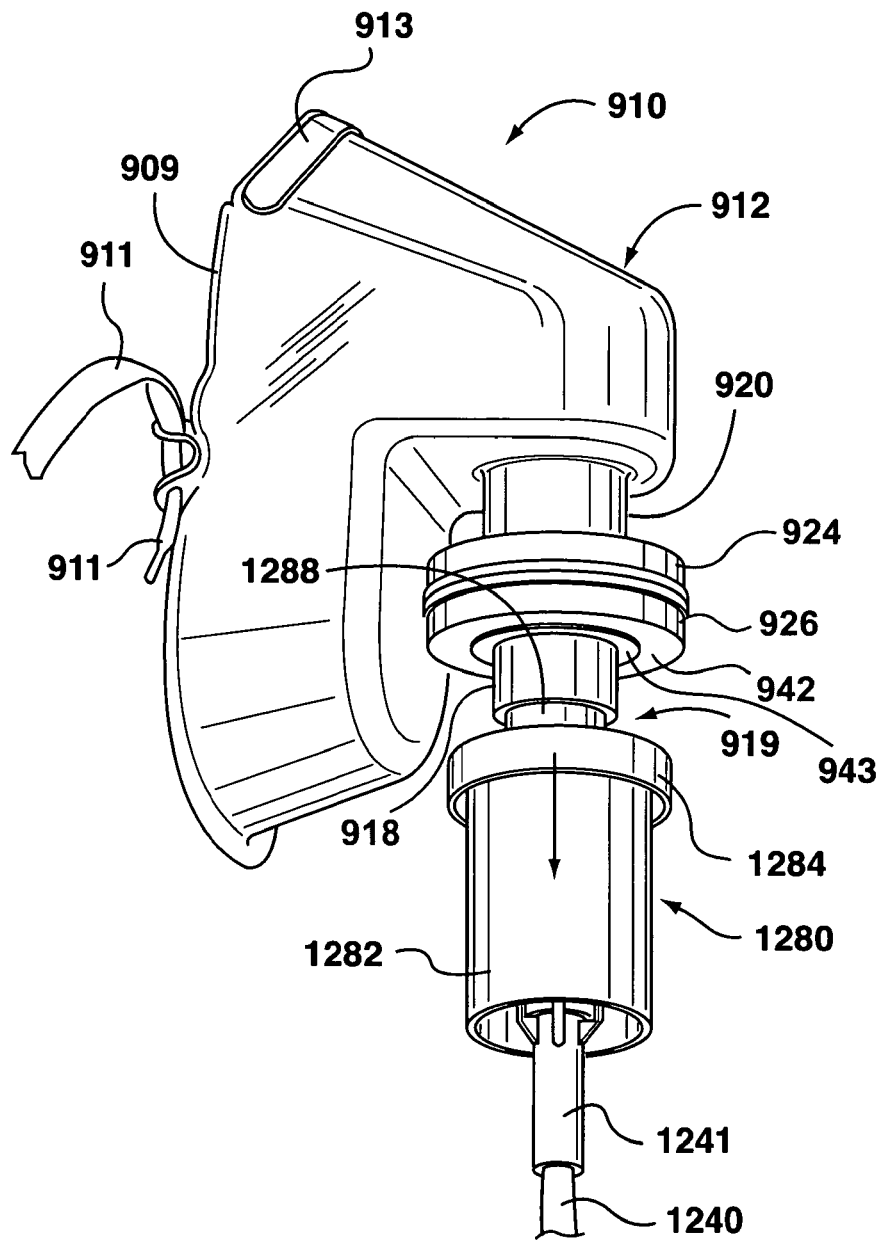
FIG. 12A shows a second exemplary nebulizer according to an aspect of the present invention, detachably secured to the therapeutic face mask of FIG. 9.
Figure 12B:
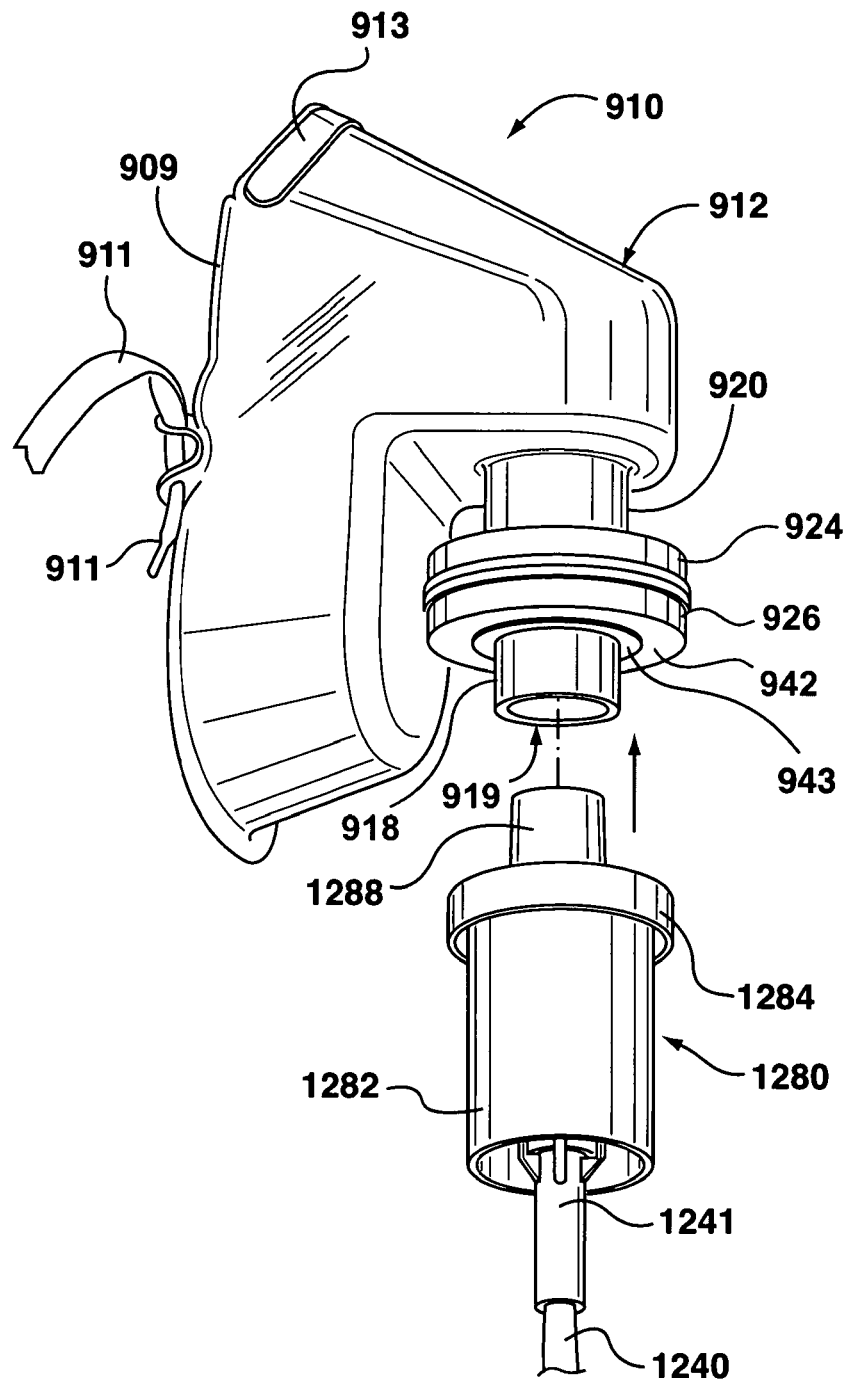
FIG. 12B shows a second exemplary nebulizer according to an aspect of the present invention, detached from the therapeutic face mask of FIG. 9.

As shown in FIGS. 12A and 12B, the treatment attachment is a nebulizer. FIG. 12A shows a nebulizer 1280 detachably mounted on the treatment-receiving end 919 of the connector 914, and FIG. 11B shows the nebulizer 1280 detached therefrom. Like the nebulizer 680, the nebulizer 1280 shown in FIGS. 12A and 12B comprises a medication cup 1282 for containing liquid medication, and a removable cap 1284. A tube attachment member (not shown) for detachably receiving one end 1241 of an oxygen (or oxygen/air mixture) supply tube 1240 extends downwardly to define a fluid communication path from the supply tube into the medication cup 1282. The cap 1284 has an upwardly extending neck 1288 which is shaped for removable attachment of the nebulizer 1280 to a mating connector of a therapeutic face mask, in this case the lower tubular body portion 918 defining the treatment-receiving end 919 of the connector 914. In particular, the upwardly extending neck 1288 has an outer diameter corresponding to the inner diameter of the lower tubular body portion 918 defining the treatment-receiving end 919 of the connector 914, enabling a friction fit of the upwardly extending neck 1288 within the treatment-receiving end 919 of the connector 914. As with the nebulizer 680, the particular details of the operation of nebulizing or atomizing structure of the nebulizer 1280 are outside the scope of the present invention.

Referring again to FIG. 9, when the face-engaging portion 912 has been placed over the patient's mouth and nose, with either an oxygen reservoir bag 1136 (FIGS. 11A and 11B) or a nebulizer 1280 (FIGS. 12A and 12B) in place and connected to a supply of oxygen or oxygen/air mixture, inhaling by the patient will cause the inhalation valve 930 to open so that oxygen (or an oxygen/air mixture, or a medication-laden oxygen/air mixture) passes through the second passage 928, through the inhalation valve 930 and through the central aperture in the annular filter 948, to the first passage 922 and into the face-engaging portion 912 and thence into the patient's mouth and nose. The pressure of the oxygen in the second passage 928 assists with the opening of the inhalation valve 930 when the patient inhales (with consequent lowering of pressure in the first passage 922). The lower pressure in the first passage 922 causes the exhalation valve 940 to remain closed. The anti-asphyxia valve 950 also remains closed because the lower pressure in the first passage 922 is not sufficiently low to cause it to open.

When the patient exhales, the increase in pressure in the first passage 922 causes the inhalation valve 930 to close and the anti-asphyxia valve 950 to remain closed. The increase in pressure in the first passage 922 then causes the exhalation valve 940 to open so that air in the first passage 922 passes therethrough (after passing through the annular filter 948) to the external atmosphere. The filter 948 filters the air exhaled by the patient, thereby filtering not only airborne pathogens, but also filtering excess medication when a nebulizer is attached to the treatment-receiving end 919.

Such inhaling and exhaling continues while the oxygen (or oxygen/air mixture) supply to the second passage 928 is sufficient, with the oxygen reservoir bag 1136 or the nebulizer 1280 functioning in the conventional manner. If the oxygen (or oxygen/air mixture) supply ceases, so that there is little or no oxygen flow through the inhalation valve 930, further lowering of pressure in the first passage 922 produced by the patient inhaling more strongly causes the anti-asphyxia valve 950 to open. Air is then drawn through the anti-asphyxia valve 950 from the external atmosphere into the first passage 922 and hence to the patient.

Accordingly, so long as oxygen (or an oxygen/air mixture or medication-laden oxygen/air mixture) is supplied to the treatment receiving end 919 of the connector 914, the patient will inhale the supplied gas through the inhalation valve 930, and exhale through the exhalation valve 940. In addition, if a patient's peak inspiratory effort exceeds the flow rate of the supplied gas, the anti-asphyxia valve 950 will open to provide supplementary air to match the inspiratory effort. Moreover, if the gas supply to the treatment receiving end 919 of the connector 914 should cease, such as where an oxygen tank is empty, the patient can inhale normally through the anti-asphyxia valve 950 to avoid asphyxiation, and continue to exhale through the exhalation valve 940.

Thus, neither the patient nor medical personnel need to tamper with the face mask if the oxygen supply fails. Optionally, the anti-asphyxia valve 950 can be configured to include a second annular filter (not shown) to filter incoming atmospheric air.

It is to be appreciated that the relative placement of the exhalation valve 940 and the anti-asphyxia valve 950 may be reversed, with suitable minor modifications to the structure of the connector 914, without departing from the scope of the present invention.

Either of the methods 700, 800 may be performed using a therapeutic face mask such as the therapeutic face mask 910 described above.

Figure 13A:
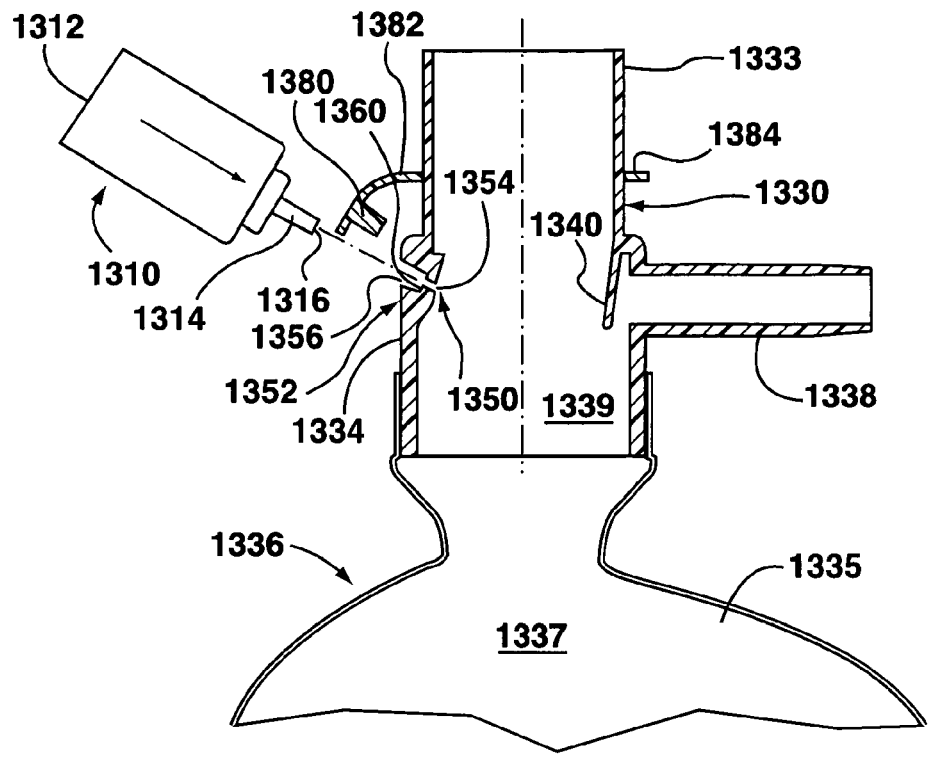
FIG. 13A is cross-sectional view of part of an oxygen reservoir therapy bag having an integral metered-dose inhaler port, also showing a metered-dose inhaler, according to an aspect of the present invention.
Figure 13B:
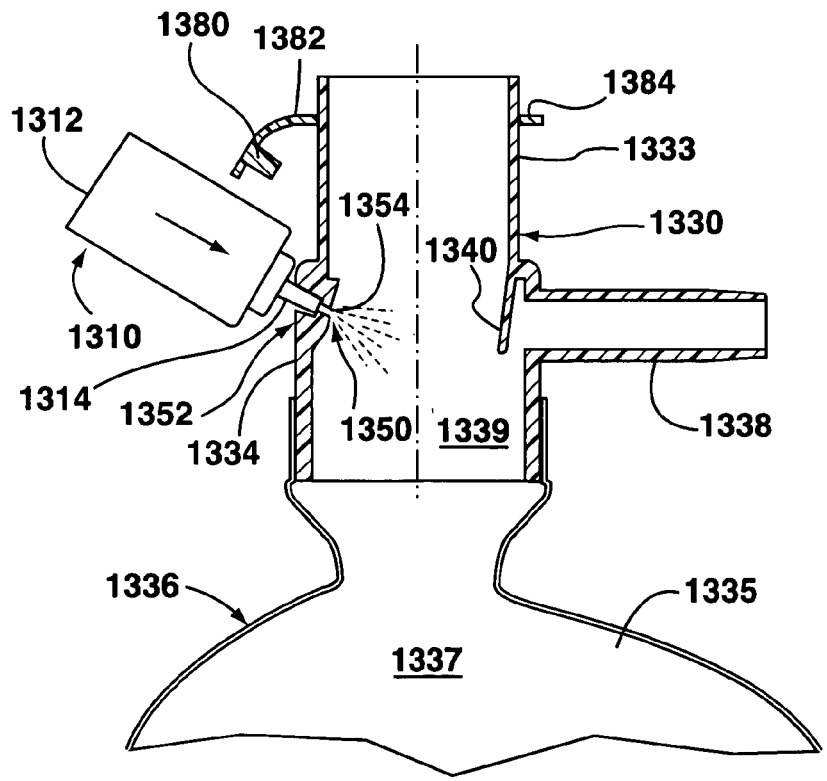
FIG. 13B is a cross-sectional showing the oxygen reservoir therapy bag portion shown in FIG. 13A, showing the metered-dose inhaler engaged with the metered-dose inhaler port.

With reference now to FIGS. 13A and 13B, according to another aspect of the present invention an oxygen therapy reservoir bag may be provided with a metered-dose inhaler port. Metered-dose inhalers are well known, and an exemplary metered-dose inhaler is indicated generally at 1310. The metered-dose inhaler 1310 comprises a container 1312, a metered valve (not shown) and an actuator tube 1314. The medication, along with a propellant, is stored in the container. As is known, when the actuator tube 1314 is moved toward the container 1312, it actuates the metered valve, thereby enabling a measured dose of aerosolized medicine to escape the container through the metered valve, and pass through the actuator tube 1314. Typical types of medication for which metered-dose inhalers are used include bronchodilators and corticosteroids.

FIG. 13 also shows an exemplary oxygen reservoir bag 1336 according to an aspect of the present invention, which also includes a metered-dose inhaler port 1350. The exemplary oxygen reservoir bag 1336 comprises a rigid neck 1330 and a flexible oxygen reservoir bag member 1335 which is sealingly secured to a lower end portion 1334 of the neck 1330 so that the interior volume 1337 of the oxygen reservoir bag member 1335 is in fluid communication with the interior volume 1339 of the neck 1330. The neck 1330 includes an open upper end portion 1333 having an outer diameter corresponding to the inner diameter of the treatment-receiving end to which it is to be coupled. For example, the exemplary oxygen reservoir bag 1336 could be coupled to either of the therapeutic face masks 210, 910, or to other therapeutic face masks constructed according to aspects of the of the present invention, or to conventional oxygen therapy face masks. Thus, the neck 1330 is shaped, by way of the upper end portion 1333, for removable coupling of the oxygen reservoir bag 1336 to a mating connector of a therapeutic face mask. A laterally extending tube attachment member 1338 for receiving an oxygen supply tube (not shown) extends outwardly from the neck 1330 and is in fluid communication with the interior volume 1339 of the neck 1330. A diffuser plate 1340 is opposed to and spaced from the tube attachment member 1338 to assist in directing the incoming oxygen (or oxygen/air mixture) from the tube attachment member 1338 into the interior volume 1337 of the oxygen reservoir bag member 1335. In the illustrated embodiment, the neck 1330 is valveless in that it does not have any valves disposed therein to govern fluid flow therethrough because the oxygen reservoir bag 1330 is to be used in conjunction with a therapeutic face mask having a connector that includes the requisite valve arrangements; it is also contemplated that a metered-dose inhaler port according to an aspect of the present invention may be provided in the neck of an oxygen reservoir bag 1330 that is permanently secured to a face-engaging portion of a therapeutic face mask and may hence include a valve.

Referring now specifically to FIG. 13A, the metered dose inhaler port 1350 is defined in the neck 1330 at a region 1352 of increased thickness. The metered dose inhaler port 1340 comprises an inner channel 1354 and an outer channel 1356, each of which is defined in the neck 1330. The inner channel 1354 is the neck in fluid communication with the interior volume 1339 of the neck of the neck 1330, and the outer channel 1356 is in fluid communication with the ambient environment. In addition, the inner and outer channels 1354, 1356 are in fluid communication with one another. As can be seen, the outer channel 1356 is larger than the inner channel 1354 so as to define a shoulder 1360 therebetween. The outer channel 1356 is sized to receive the actuator tube 1314 of the metered-dose inhaler 1310. In the illustrated embodiment, the inner channel 1354 and the outer channel 1356 are cylindrical and are coaxial with one another, so that the shoulder 1360 is an annular shoulder. However, other channel shapes may be used, and the channels 1354, 1356 may be of dissimilar shapes, and need not be coaxial. The inner channel 1354 is angled toward the oxygen reservoir bag member 1335.

Referring now to FIG. 13B, when a medication contained in a metered-dose inhaler is to be administered to a patient wearing a therapeutic face mask including an oxygen reservoir bag such as the oxygen reservoir bag 1336, the actuator tube 1314 of the metered-dose inhaler 1310 is inserted into the metered-dose inhaler port 1350 so that the annular rim 1316 (FIG. 13A) of the actuator tube 1314 engages the shoulder 1360 in the metered-dose inhaler port 1350, and the container 1312 is moved toward the neck 1330. Because the annular rim 1316 of the actuator tube 1314 engages the shoulder 1360, moving the container 1312 toward the neck 1330 results in relative movement of the actuator tube 1314 toward the container 1312, thus opening the metered valve and releasing a metered dose of medication through the actuator tube 1314. The pressure resulting from pushing the container 1312 toward the neck 1330 provides sufficient sealing between the actuator tube 1314 and the shoulder 1360 so that the medication travels from the actuator tube 1314 into the inner channel 1354. Because the inner channel 1354 is angled toward the oxygen reservoir bag member 1335, the medication is directed into interior volume 1337 of the oxygen reservoir bag member 1335 where it can disperse for inhalation by the patient.

Generally speaking, the width or diameter of the inner channel 1354 will not be large enough to result in significant leakage of oxygen (or oxygen/air mixture) from the neck 1330 to the ambient environment, or of ambient air into the neck 1330. Optionally, an oxygen reservoir bag including a metered-dose inhaler port (such as oxygen reservoir bag 1330) may be provided with a cap for selectively sealing the metered-dose inhaler port 1330. As shown in FIGS. 13A and 13B, the oxygen reservoir bag 1330 is provided with a cap arrangement which includes a cap 1380 which can be removably sealingly received in the outer channel 1356 (e.g. by a friction fit) and which is secured by a flexible attachment member 1382 to a ring 1384 which surrounds the upper end portion 1333 of the neck 1330.

Therapeutic face masks constructed in accordance with aspects of the present invention, such as the exemplary therapeutic face masks 210, 910, can support a closed isolation system, which inhibits escape of supplied oxygen or oxygen/air mixture through the exhalation ports, and can also direct exhalation to pass through a suitable filter to reduce the risk of transmitting infection by way of airborne pathogens or contaminated water droplets entrained in the exhaled air. When a suitable filter made from an appropriate filtrate is used with therapeutic face masks constructed in accordance with aspects of the present invention, a therapeutic face mask such as the therapeutic face mask 210, 910 assists in maintaining respiratory isolation of a patient during oxygen and drug aerosol therapy, and can thereby reduce the risk of airborne infections.

Therapeutic face masks according to aspects of the present invention may come in a variety of sizes to enable a good fit of the face-engaging portion thereof. For example, there may be provided a "large adult" size, "small adult" size, and "child" size, or other types of sizes, for either of the exemplary therapeutic face masks 210, 910, or for other therapeutic face masks according to aspects of the present invention.

Preferably, the face-engaging portions 212, 912 are constructed from flexible PVC, to facilitate adjustment to individual facial features, and the connectors, such as connectors 214 and 915, and the necks, such as necks 530, 688, 1130, 1288 of the oxygen reservoir bags 536, 1136 and nebulizers 680, 1280, are made from rigid PVC. Preferably, the PVC material is a transparent or translucent PVC material. The valve diaphragms, such as diaphragms 252, 256, 932, 942, 952, are preferably made from a suitable silicone material. All of the components of therapeutic face masks according to aspects of the present invention are preferably constructed from latex-free materials, so as to avoid triggering an allergic reaction in patients having latex allergies, and are disposable for hygienic reasons. Preferably, filters used in accordance with aspects of the present invention, such as filters 276, 948, are HEPA-rated, submicron, hydrophobic filters capable of effectively filtering bacteria and viruses. Suitable filter materials are available from 3M, which has a corporate headquarters address at 3M Corporate Headquarters, 3M Center, St. Paul, Minn. 55144-1000.

A single therapeutic face mask incorporating connectors according to various aspects of the present invention can function as a low oxygen mask, a medium oxygen mask, a high oxygen (i.e. from 30% to 90% oxygen concentrations) mask and a nebulizer mask, obviating the need for multiple masks and thereby resulting in cost savings.

The advantages of the present invention will now be readily apparent to a person skilled in the art from the above description of a preferred embodiment thereof. Other advantages and embodiments will also be now readily apparent.

What is claimed is:
1. A therapeutic face mask, comprising:
a face-engaging portion having a fluid aperture;
only a single connector, the connector having a mask-engaging end and only a single treatment-receiving end, the connector defining a fluid passageway between the mask-engaging end and the treatment-receiving end thereof, wherein:
the mask-engaging end of the connector is coupled to the face-engaging portion in fluid communication with the fluid aperture;
the connector has only a single attachment mounting for detachably sealingly receiving a treatment attachment in fluid communication therewith, the attachment mounting being defined at the treatment-receiving end of the connector; and
the connector has at least one inhalation valve interposed in the fluid passageway between the mask-engaging end and the treatment-receiving end thereof, each inhalation valve being a one-way valve and being oriented to permit fluid flow from the treatment-receiving end to the mask-engaging end during inhalation and to inhibit fluid flow from the mask-engaging end to the treatment-receiving end;
at least one anti-asphyxia valve assembly configured to permit fluid flow therethrough from ambient to the face-engaging portion during inhalation only when fluid flow to the treatment-receiving end of the connector is less than inspiratory effort during inhalation; and
at least one valve-governed exhalation port in fluid communication with the face-engaging portion and positioned to define an exhalation path from the face-engaging portion to ambient which bypasses the inhalation valve and which permits fluid flow from the face-engaging portion to ambient during exhalation and inhibits fluid flow from ambient to the face engaging portion at least when fluid flow to the treatment-receiving end of the connector exceeds inspiratory effort during inhalation;
wherein each exhalation port is defined in the connector and is in fluid communication with the face-engaging portion by way of the fluid passageway, and wherein each exhalation port is positioned between the inhalation valve and the mask-engaging end of the connector;
wherein each anti-asphyxia valve assembly comprises a single anti-asphyxia valve disposed in a corresponding exhalation port and oriented to:
permit fluid flow from the connector to ambient through the exhalation port during exhalation; and
permit fluid flow from ambient to the connector through the exhalation port during inhalation only when fluid flow to the treatment-receiving end of the connector is less than ins inspiratory effort during inhalation; and wherein each anti-asphyxia valve comprises an aperture having a single cross member extending thereacross, and a flexible diaphragm secured to the cross member on an outer side of the cross member relative to the fluid passageway.

2. A connector for a therapeutic face mask, the connector having:
a mask-engaging end securable to a face-engaging portion of the therapeutic face mask in fluid communication with a fluid aperture of the face-engaging portion;
a treatment-receiving end;
a fluid passageway defined between the end and the treatment-receiving end; only a single attachment mounting for detachably sealingly receiving a treatment attachment in fluid communication with the fluid passageway, the attachment mounting being defined at the treatment-receiving end;
at least one inhalation valve interposed in the fluid passageway between the mask-engaging end and the treatment-receiving end of the connector, each inhalation valve being a one-way valve and being oriented to permit fluid flow from the treatment-receiving end through the mask-engaging end during inhalation and to inhibit fluid flow from the mask-engaging end through the treatment-receiving end; and
at least one anti-asphyxia valve assembly configured to permit fluid flow therethrough from ambient to the face-engaging portion during inhalation only when fluid flow to the treatment-receiving end of the connector is less than inspiratory effort during inhalation;
at least one valve-governed exhalation port in fluid communication with the face-engaging portion and positioned to define an exhalation path from the face-engaging portion to ambient which bypasses the inhalation valve and which permits fluid flow from the face-engaging portion to ambient during exhalation and inhibits fluid flow from ambient to the face engaging portion at least when fluid flow to the treatment-receiving end of the connector exceeds inspiratory effort during inhalation;
wherein each anti-asphyxia valve assembly comprises a single anti-asphyxia valve disposed in a corresponding exhalation port and oriented to:
permit fluid flow from the connector to ambient through the exhalation port during exhalation; and
permit fluid flow from ambient to the connector through the exhalation port during inhalation only when fluid flow to the treatment-receiving and of the connector is less than inspiratory effort during inhalation;

wherein each anti-asphyxia valve comprises an aperture having a single cross member extending thereacross, and a flexible diaphragm secured to the cross member on an outer side of the cross member relative to the fluid passageway.

3. An oxygen therapy face mask, comprising:
a face-engaging portion having an inlet passage through which oxygen from a pressurized source can be received;
a valve assembly connected to the inlet passage having a first one-way valve operable to permit flow of oxygen from a source thereof to a patient and inhibit flow in the opposite direction, the valve assembly also having an inlet/outlet passageway with a two-way valve permitting ambient air to flow to the patient and permitting exhaled air to flow from the patient to the ambient atmosphere;
wherein the two-way valve comprises a rod-like support member extending across the inlet/outlet passage and a diaphragm mounted on the support member and having a closed position blocking air flow through the inlet/outlet valve, the diaphragm being bendable by air pressure from either side thereof to enable air to flow through the valve from the higher pressure side of the diaphragm to the lower pressure side thereof.

4. The oxygen therapy face mask of claim 3, wherein the valve assembly has a first tubular inlet portion to which an oxygen reservoir bag may be detachably connected, the first tubular inlet portion also being capable of detachably receiving, in the absence of the oxygen reservoir bag, a medication supplying nebulizer, whereby medication can be supplied by the nebulizer through the one-way valve into the face-engaging portion for passage to the patient.

5. The oxygen therapy face mask of claim 4, wherein the inlet/outlet passage has a tubular portion connecting the two-way valve with the ambient atmosphere, the tubular portion being capable of detachably receiving a filter assembly operable to filter air passing from the ambient atmosphere to the two-way valve and from the two-way valve to the ambient atmosphere.

6. The oxygen therapy face mask of claim 3, wherein the inlet/outlet passage has a tubular portion connecting the two-way valve with the ambient atmosphere, the tubular portion being capable of detachably receiving a filter assembly operable to filter air passing from the ambient atmosphere to the two-way valve and from the two-way valve to the ambient atmosphere.

* * * * *